US006271204B1

(12) United States Patent
Rademacher et al.

(10) Patent No.: US 6,271,204 B1
(45) Date of Patent: Aug. 7, 2001

(54) CYCLITOL CONTAINING CARBOHYDRATES FROM HUMAN TISSUE WHICH REGULATE GLYCOGEN METABOLISM

(75) Inventors: Thomas William Rademacher, Oxford; Hugo Caro, Herts, both of (GB)

(73) Assignee: Rademacher Group Limited, London (GB)

(*) Notice: Subject to any disclaimer, the term of this patent is extended or adjusted under 35 U.S.C. 154(b) by 0 days.

(21) Appl. No.: 09/254,748

(22) PCT Filed: Sep. 11, 1997

(86) PCT No.: PCT/GB97/02533

§ 371 Date: Jun. 14, 1999

§ 102(e) Date: Jun. 14, 1999

(87) PCT Pub. No.: WO98/11117

PCT Pub. Date: Mar. 19, 1998

(30) Foreign Application Priority Data

Sep. 11, 1996 (GB) .................................................. 9618929

(51) Int. Cl.[7] .................................................. A61K 31/715

(52) U.S. Cl. .................................. 514/25; 514/8; 514/54; 514/61; 536/4.1; 536/17.2; 536/18.7; 536/123.1

(58) Field of Search .................................. 536/4.1, 17.2, 536/18.7, 123.1; 514/8, 25, 54, 61

(56) References Cited

U.S. PATENT DOCUMENTS

| 4,839,466 | 6/1989 | Saltiel ................................. 530/395 |
| 4,906,468 | 3/1990 | Saltiel ................................. 424/85.8 |
| 5,122,603 | 6/1992 | Larner et al. ........................ 536/18.7 |

FOREIGN PATENT DOCUMENTS

| 0 532 915 A2 | 8/1992 | (EP) ................................. C07K/9/00 |
| WO 96/29425 | 9/1996 | (WO) . |

OTHER PUBLICATIONS

Caro, H.N. et al., "Isolation and Partial Characterisation of Insulin–Mimetic Inositol Phosphoglycans from Human Liver," 61(2) *Biochemical and Molecular Medicine* 214–228 (Aug. 1997).
Farese, R. et al., "Insulin–Induced Activation of Glycerol–3–Phosphate Acyltransferase by a chiro–Inositol–Containing Insulin Mediator is Defective in Adipocytes of Insulin–Resistant, Type II Diabetic, Goto–Kakizaki Rats," 91 *Proc. Natl. Acad. Sci.* 11040–11044 (Nov. 1994).
Fonteles, M. et al. "Infusion of pH 2.0 D–chiro–Inositol Glycan Insulin Putative Mediator Normalizes Plasma Glucose in Streptozotocin Diabetic Rats at a Dose Equivalent to Insulin Without Inducing Hypoglycaemia," 39 *Diabetologica* 731–734 (1996).

Huang, L. et al., "Chiroinositol Deficiency and Insulin Resistance. III. Acute Glycogenic and Hypoglycemic Effects of Two Inositol Phosphoglycan Insulin Mediators in Normal and Streptozotocin–Diabetic Rats in Vivo*," 132(2) *Endocrinology* 652–657 (1993).
Kennington, A. et al., "Low Urinary chiro–Inositol Excretion in Non–Insulin–Dependent Diabetes Mellitus," 323(6) *The New England Journal of Medicine* 373–378 (1990).
Kunjara S. et al., "Tissue Specific Release of Inositol Phophoglycans," in *Biopolymers and Bioproducts: Structure, Function, and Applications*, J. Svast et al. (ed), Dokya Publications, 301–306 (1995).
Lazar, D. et al. "Stimulation of Glycogen Synthesis by Insulin in Human Erythroleukemia Cells Requires the Synthesis of Glycosyl–Phophatidylinositol," 91 *Proc. Natl. Acad. Sci.* 9665–9669 (Oct. 1994).
Macaulay, S. and Larkins, R. "Impaired Insulin Action in Adipocytes of New Zealand Obese Mice: A Role for Postbinding Defects in Pyruvate Dehydrogenase and Insulin Mediator Activity," 37(10) *Metabolism* 958–965 (Oct. 1988).
Macaulay, S. et al., "Correlation of Insulin Receptor Level with Both Insulin Action and Breakdown of a Potential Insulin Mediator Precursor; Studies in CHO Cell–Lines Transfected with Insulin Receptor cDNA," 1134 *Biochimica et Biophysica Acta* 53–60 (1992).
Malchoff, C. et al., "A Putative Mediator of Insulin Action Which Inhibits Adenylate Cyclase and Adenosine 3',5' – Monophosate–Dependent Protein Kinase: Partial Purification from Rat Liver: Site and Kinetic Mechanism of Action*," 120(4) *Endocrinology* 1327–1337 (Apr. 1987).
Monuki, E. et al., "Cell–Specific Action and Mutable Structure of a Transcription Factor Effector Domain," 90 *Proc. Natl. Acad. Sci.* 9978–9982 (Nov. 1993).
Nestler, J. et al., "Insulin Mediators are the Signal Transduction System Responsible for Insulin's Actions on Human Placental Steroidogenesis," 129(6) *Endocrinology* 2951–2956 (1991).
Ortmeyer, H. et al., "Chiroinositol Deficiency and Insulin Resistance. I. Urinary Excretion Rate of Chiroinositol Is Directly Associated with Insulin Resistance in Spontaneously Diabetic Rhesus Monkeys," 132(2) *Endocrinology* 640–645 (1993).
Ortmeyer, H. et al., "Chiroinositol Deficiency and Insulin Resistance. II. Acute Effects of D–Chiroinositol Administration in Streptozotocin–Diabetic Rats, Normal Rats Given a Glucose Load, and Spontaneously Insulin–Resistant Rhesus Monkeys," 132(2) *Endocrinology* 646–651 (1993).
Ostlund, R. et al., "D–chiro–Inositol metabolism in diabetes mellitus," 90 *Proc. Natl. Acad. Sci USA* 9988–9992 (Nov. 1993).

(List continued on next page.)

*Primary Examiner*—Kathleen K. Fonda
(74) *Attorney, Agent, or Firm*—Emily M. Haliday; Skjerven Morrill MacPherson LLP

(57) ABSTRACT

The present invention provides for an isolated P-type substance having a structure identical to a P-type substance obtained from human liver or placenta, which is a cyclitol containing carbohydrate comprising $Mn^{2+}$ and $Zn^{2+}$ and related compositions.

23 Claims, 10 Drawing Sheets

OTHER PUBLICATIONS

Rademacher, T. et al., "Inositolphosphoglycan Second Messengers," 27 *Brazilian J. Med. Biol. Res.* 327–341 (1994).

Represa, J. et al., "Glycosyl–Phosphatidylinositol/Inositol Phosphoglycan: A Signaling System for the Low–Affinity Nerve Growth Factor Receptor," 88 *Proc. Natl. Acad. Sci.* 8016–8109 (Sep. 1991).

Romero, G. et al. "Anti–Inositolglycan Antibodies Selectively Block Some of the Actions of Insulin in Intact $BC_3H1$ Cells," 87 *Proc. Natl. Acad. Sci.* 1476–1480 (Feb. 1990).

Suzuki, S. et al. "Urinary chiro–Inositol Excretion is an Index Marker of Insulin Sensitivity in Japanese Type II Diabetes," 17(12) *Diabetes Care* 1465–1468 (Dec. 1994).

Villalba, M. et al. "Hydrolysis of Glycosyl–Phophatidylinositol in Response to Insulin is Reduced in Cells Bearing Kinase–Deficient Insulin Receptors," 2 *Growth Factors* 91–97 (1990).

Villalba, M. et al., "Inhibition of cyclic AMP–dependent protein kinase by the polar head group of an insulin–sensitive glycophospholipid," 968 *Biochimica et Biophysica Acta* 69–76 (1988).

Fig.2.
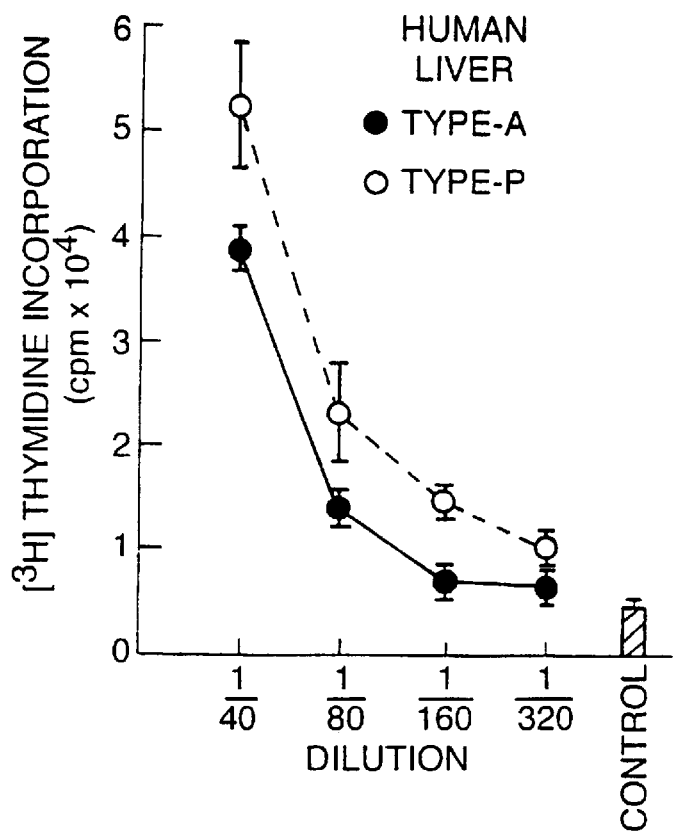
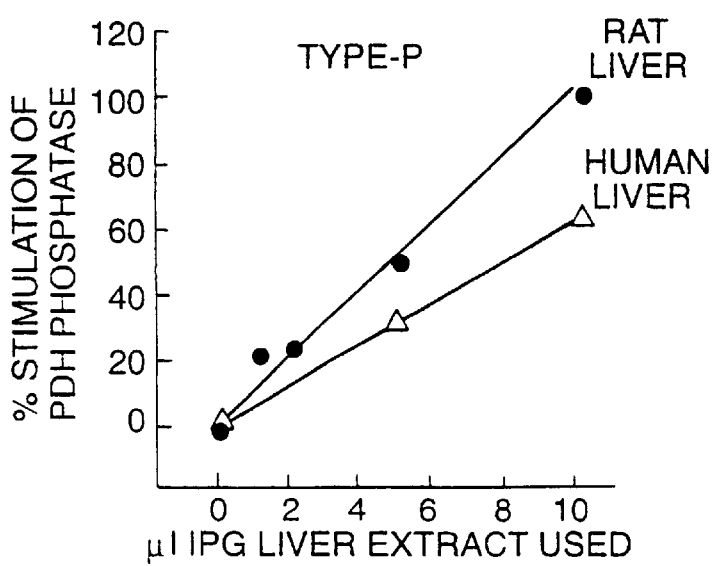

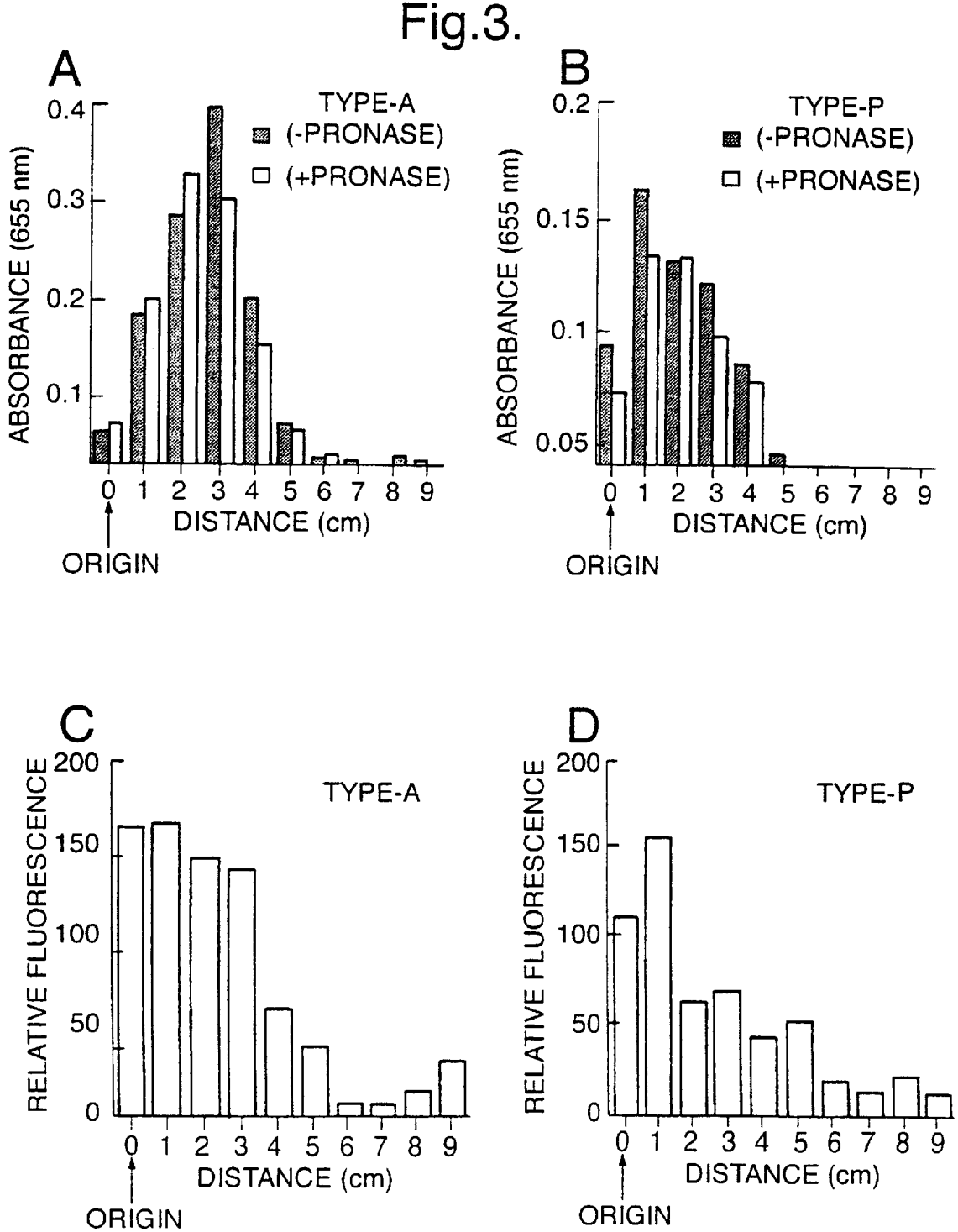

Fig. 5.
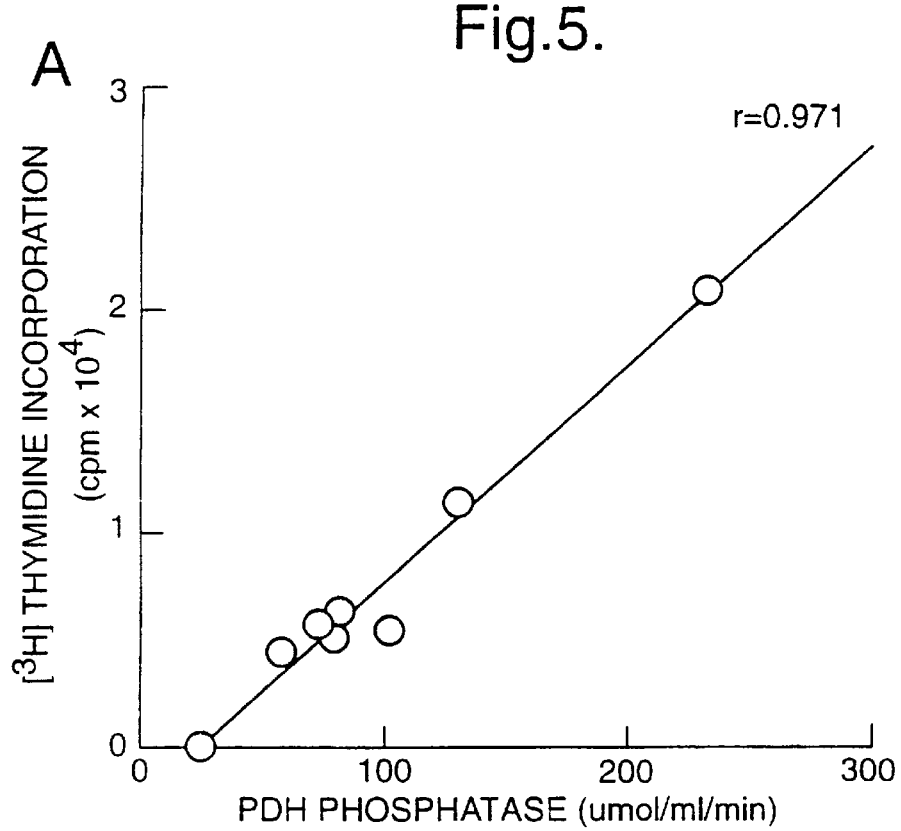
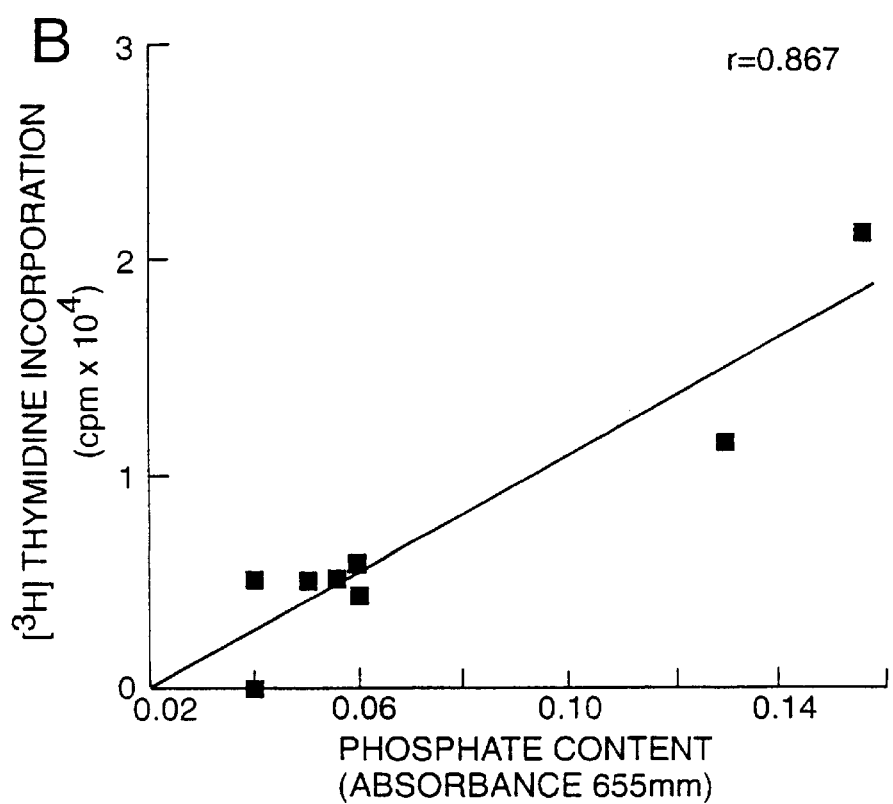

CYCLITOL CONTAINING CARBOHYDRATES FROM HUMAN TISSUE WHICH REGULATE GLYCOGEN METABOLISM

This is the U.S. National Stage entry under 35 U.S.C. 371 of PCT/GB97/02533, filed Sep. 11, 1997.

FIELD OF THE INVENTION

The present invention relates to the characterisation of second messengers of insulin and other growth factors that regulate glycogen metabolism. In particular, the present invention relates to substances which are cyclitol containing carbohydrates, said substances containing $Mn^{2+}$ and/or $Zn^{2+}$ ions, to cyclitol containing carbohydrates as obtainable from human liver or human placenta, to compositions comprising these substances, and to the uses of these substances.

BACKGROUND OF THE INVENTION

Many of the actions of growth factors on cells are thought to be mediated by a family of inositol phosphoglycan (IPG) second messengers (T W Rademacher at al, Brazilian J. Med Biol. Res., 27, 327–341, (1994)). It is thought that the source of IPGs is a "free" form of glycosyl phosphatidylinositol (GPI) situated in cell membranes. IPGs are thought to be released by the action of phosphatidylinositol-specific phospholipases following ligation of growth factor to receptors on the cell surface.

There is evidence that IPGs mediate the action of a large number of growth factors including insulin, nerve growth factor, hepatocyte growth factor, insulin-like growth factor I (IGF-I), fibroblast growth factor, transforming growth factor β, the action of IL-2 on B-cells and T-cells, ACTH signalling of adrenocortical cells, IgE, FSH and hCG stimulation of granulosa cells, thyrotropin stimulation of thyroid cells, cell proliferation in the early developing ear and rat mammary gland. However, to date, most of the research in this area has concentrated on the second messengers released by cells in response to insulin. For example, insulin stimulates rapid hydrolysis of membrane-associated GPI molecules in myocytes, adipocytes, hepatoma cells and T-cells. Recently, it has become clear that, at least where insulin is concerned, the released IPGs play an essential role as second messengers, and can in fact mimic many of the effects of insulin in the absence of the hormone.

Soluble IPG fractions have been obtained from a variety of animal tissues including rat tissues (liver, kidney, muscle brain, adipose, heart) and bovine liver. IPG biological activity has also been detected in malaria parasitized RBC and mycobacteria. The ability of an anti-inositolglycan antibody to inhibit insulin action on human placental cytotrophoblasts and BC3H1 myocytes or bovine-derived IPG action on rat diaphragm and chick ganglia suggests cross-species conservation of some three-dimensional features. However, it is well established that species-specific glycoconjugates are a common characteristic and structural characteristics determined on non-human derived IPG may not be found on the human derived material.

We have divided the family of IPG second messengers into distinct A and P-type subfamilies on the basis of their biological activities. In the rat, release of the A and P-type mediators has been shown to be tissue-specific (Kunjara et al, Biopolymers and Bioproducts: Structure, Function and Applications, J. Svast et al (ed), Dokya Publications, 301–306, (1995)). Although in the past it has not been possible to isolate single purified components from the tissue derived IPG fractions, much less in sufficient quantities to allow structural characterisation, there have been studies of the biological activities of the IPG containing fractions, and speculation as to the identity of the active components from non-human sources of the fractions based on indirect evidence from metabolic labelling and cleavage techniques.

Biological activity studies have shown that A-type mediators modulate the activity of a number of insulin-dependent metabolic effects such as acetylCoA carboxylase (activates), cAMP dependent protein kinase (inhibits), adenylate cyclase (inhibits) and cAMP phosphodiesterases (stimulates). In contrast, P-type mediators modulate the activity of enzymes such as pyruvate dehydrogenase phosphatase (stimulates) and glycogen synthase phosphatase (stimulates). The A-type mediators mimic the lipogenic activity of insulin on adipocytes, whereas the P-type mediators mimic the glycogenic activity of insulin on muscle. Both A and P-type mediators are mitogenic when added to fibroblasts in serum free media. The ability of the mediators to stimulate fibroblast proliferation is enhanced if the cells are transfected with the EGF-receptor. A-type mediators can stimulate cell proliferation in chick cochleovestibular ganglia.

Despite these studies, evidence for the presence of a family of soluble IPG-type mediators in a primary target organ for insulin action in humans has not yet been established. Further, research in this area has been severely hampered by the limited availability of the A and P-type IPGs in fractions derived from mammalian tissues. In particular, there have been experimental difficulties in identifying, isolating and characterising the active components of the IPG fractions having A- and P-type biological activity.

Thus, studies on the measurement in urine of chiro and myo inositol have been complicated by the fact that both breakdown of endogenous IPGs and dietary sources of the sugars will be present. Accordingly, prior art studies in this area which assumed that the P-type mediator contains chiro-inositol and that the A-type mediator contains myo-inositol must be interpreted with caution, see Fonteles, M C, Huang, L C, Larner, J, Diabetologia, 39:731–734, (1996), in which the authors report that they incorrectly identified the inositol in the P-type mediator which is pinitol and not chiro-inositol. As pinitol is not converted to chiro-inositol by the acid conditions used in carbohydrate analysis, this is a case of misidentification.

Further, analysis of material isolated by metabolic labelling with radionuclides or post-isolation labelling of extracted material cannot be related to the chemical active substance, since one is only following the labelled material and the actual active substance could co-isolate but not be labelled. In addition, various enzymic or chemical treatments of the compounds used to determine structural characteristics inactivate the compound making further structural steps impossible since one can no longer relate activity and structure. Further, as the active components of the A- and P-type IPG fractions are believed to be carbohydrates rather than proteins, they cannot be produced by recombinant DNA technology.

Thus, while there has been speculation in the art as to the chemical identity of these components, to date, there has been no isolation of an active component and no demonstration that it has A- or P-type biological activity.

SUMMARY OF THE INVENTION

Our purification reported here from human tissues generates a non-radiolabelled compound which can be visualised on Dionex chromatography and by mass spectrometry. In rats, we can relate changes in the amount of compound present to the insulin stimulation of the tissue. As the rat compounds were isolated by the same protocol as that used to isolate the human compounds, by analogy, the human substances described here are released in response to insulin stimulation. This defines them as insulin-responsive compounds. We have also purified P-type fractions using Vydac HPLC chromatography and shown that the compounds obtained have P-type biological activity.

Broadly, the present invention is based on the isolation of an active component of a P-type fraction derived from human liver or placenta in sufficient quantity to characterise this P-type substance for the first time. In particular, this characterisation showed that this substance contains metal ions, in particular $Mn^{2+}$ and/or $Zn^{2+}$, and has a biological activity associated with P-type IPG fractions, namely the property of activating pyruvate dehydrogenase (PDH) phosphatase.

Accordingly, in one aspect, the present invention provides a P-type substance which is a cyclitol containing carbohydrate, said substance containing $Mn^{2+}$ and/or $Zn^{2+}$ ions and optionally phosphate. This finding was made as some P-type fractions isolated using Vydac HPLC chromatography did not contain phosphate but were biologcially active, indicating that phosphate is not essential for biological activity.

Accordingly, in the present application, references to "inositolphosphoglycans" or "IPGs" include compounds in which phosphate is not present. These compounds are alternatively be termed inositolglycans (IGs).

We have further found the P-type substance to have the following properties:

1. Migrates near the origin in descending paper chromatography using 4/1/1 butanol/ethanol/water as a solvent.
2. Some of the P-type substances contain phosphate which is directly related to activity.
3. The free GPI precursors are resistant to cleavage by GPI-PLC from bacterial sources.
4. They are partially retained on C-18 affinity resin (Table 1).
5. They are bound on Dowex AG50 (H+) cation exchange resin (Table 1).
6. They are bound on an AG3A anion exchange resin (Table 1).
7. The activity is resistant to pronase.
8. They are detected using a Dionex chromatography system or Vydac HPLC chromatography (see FIGS. 7 to 9).

The substance may also have one or more of the following activities associated with P-type IPG fractions:

(a) stimulates the activity of glycogen synthase phosphatase;
(b) mitogenic when added to fibroblasts in serum free medium;
(c) stimulates pyruvate dehydrogenase phosphatase.

Thus, while the prior art discloses that the biological activities associated with P-type IPG can be detected in fractions obtained from bovine and rat tissues, it does not isolate or characterise the component from the fraction and demonstrate that it has a P-type IPG biological activity.

In a further aspect, the present invention provides a substance which is a cyclitol containing carbohydrate, said substance containing $Mn^{2+}$ and/or $Zn^{2+}$ ions and optionally phosphate, as obtainable by from human liver or placenta:

(a) making an extract by heat and acid treatment of a liver homogenate, the homogenate being processed from tissue immediately frozen in liquid nitrogen;
(b) after centrifugation and charcoal treatment, allowing the resulting solution to interact overnight with an AG1-X8 (formate form) anion exchange resin;
(c) collecting a fraction having P-type IPG activity obtained by eluting the column with 10 mM HCl;
(d) neutralising to pH 4 (not to exceed pH 7.8) and lyophilising the fraction to isolate the substance;
(e) descending paper chromatography using 4/1/1 butanol/ethanol/water as solvent;
(f) purification using high-voltage paper electrophoresis in pyridine/acetic acid/water; and,
(g) purification using Dionex anion exchange chromatography, or purification and isolation using Vydac HPLC chromatography to obtain the isolated P-type substance.

In a further aspect, the present invention provides an isolated substance which is a P-type cyclitol containing carbohydrate comprising $Mn^{2+}$ and $Zn^{2+}$ ions and has the biological activity of activating pyruvate dehydrogenase (PDH) phosphatase, wherein the substance has a molecular weight determined using negative mode MALDI mass spectroscopy as shown in FIG. 11, or a molecular weight related to one of the molecular weights set out in FIG. 11 by the addition or substraction of one or more 236 m/z structure units.

In a further aspect, the present invention provides pharmaceutical compositions comprising a P-type substance as described above, optionally in combination with insulin or an A-type substance for simultaneous or sequential administration. These compositions can be used in the treatment of disorders in which the glycogenic activity of patient has in some way been impaired, e.g. in obese NIDDM patients who do not produce enough P-type IPG, compared to A-type production, i.e. the ratio of A- and P-type IPGs in these patients is out of balance.

A detailed discussion on the cell signalling arrangements and the release of IPG second messengers in response to growth factors is provided in our co-pending International patent application number PCT/GB96/00669 filed on Mar. 20, 1996.

In a further aspect, the present invention provides antagonists to the substances described above and pharmaceutical compositions comprising these antagonists. These compositions can be useful in the treatment of conditions in which P-type IPGs are overproduced and/or to antagonise one of the activities of the P-type IPGs. Such an antagonists may be a related IPG which is able to compete with the P-type IPG but have no biological action in its own right. For example, the dephosphorylated form of the P-type IPG which has reduced bioactivity could compete with the active phosphorylated P-type for uptake into the cell.

In a further aspect, the present invention provides a substance or antagonist as described above for use in a method of medical treatment.

It is expected that synthetic compounds containing all or part of the active substituents of the P-type IPG could be useful as therapeutics.

BRIEF DESCRIPTION OF THE DRAWINGS

FIG. 2 shows the stimulation of EGFR T17 fibroblasts and PDH phosphatase. Panel A: Serial dilutions of stock human liver derived type-A and type-P were assayed for their ability to stimulate proliferation. Control represents the proliferation of the fibroblasts in serum-free medium with addition of IPG. Panel B: Stimulation of bovine heart derived PDH phosphatase was linear for both human and rat derived type-P mediator. The amount of mediator used was volume of stock (see Materials and Methods).

FIG. 3 shows the purification of IPG by descending paper chromatography. Descending paper chromatography profiles of control- and pronase E-treated IPG type-A and type-P, panels A and B respectively, following analysis for phosphate content. Panels C and D show the free amino groups analysis in the same chromatographic fractions. For clarity, only the first 10 fractions are displayed in each panel for pronase treated samples. The profiles for untreated mediators was identical. The solvent front was +35 cm.

FIG. 4a shows a representative electrophoretogram of IPG type-P (black) HVE following detection of phosphate. FIG. 4b shows the effect of selected fractions of IPG type-P on cell proliferation after pronase treatment, descending paper chromatography and HVE purification steps. FIG. 4b shows the effect of crude preparation of IPG type-A and IPG type-P at a final dilution of ⅟₈₀ on [$^3$H]thymidine incorporation into EGFR T17 fibroblasts. The migration positions of bromophenol blue (BB), inositol monophosphate (IP1) and inositol di/tri-phosphate are indicated by arrows.

FIG. 5 shows the correlation between [$^3$H] thymidine incorporation, PDH phosphatase stimulating activity and phosphate content of selected fractions from the HVE electrophoretogram. Panel A: HVE fractions were assayed for their ability to stimulate PDH phosphatase. The correlation between both effects was r=0.97. Panel B shows the correlation (r=0.87) between phosphate content and the stimulation by the same fractions of [$^3$H]thymidine incorporation into EGFR T17 fibroblasts.

DETAILED DESCRIPTION

Mimetic Design

Figure 1:
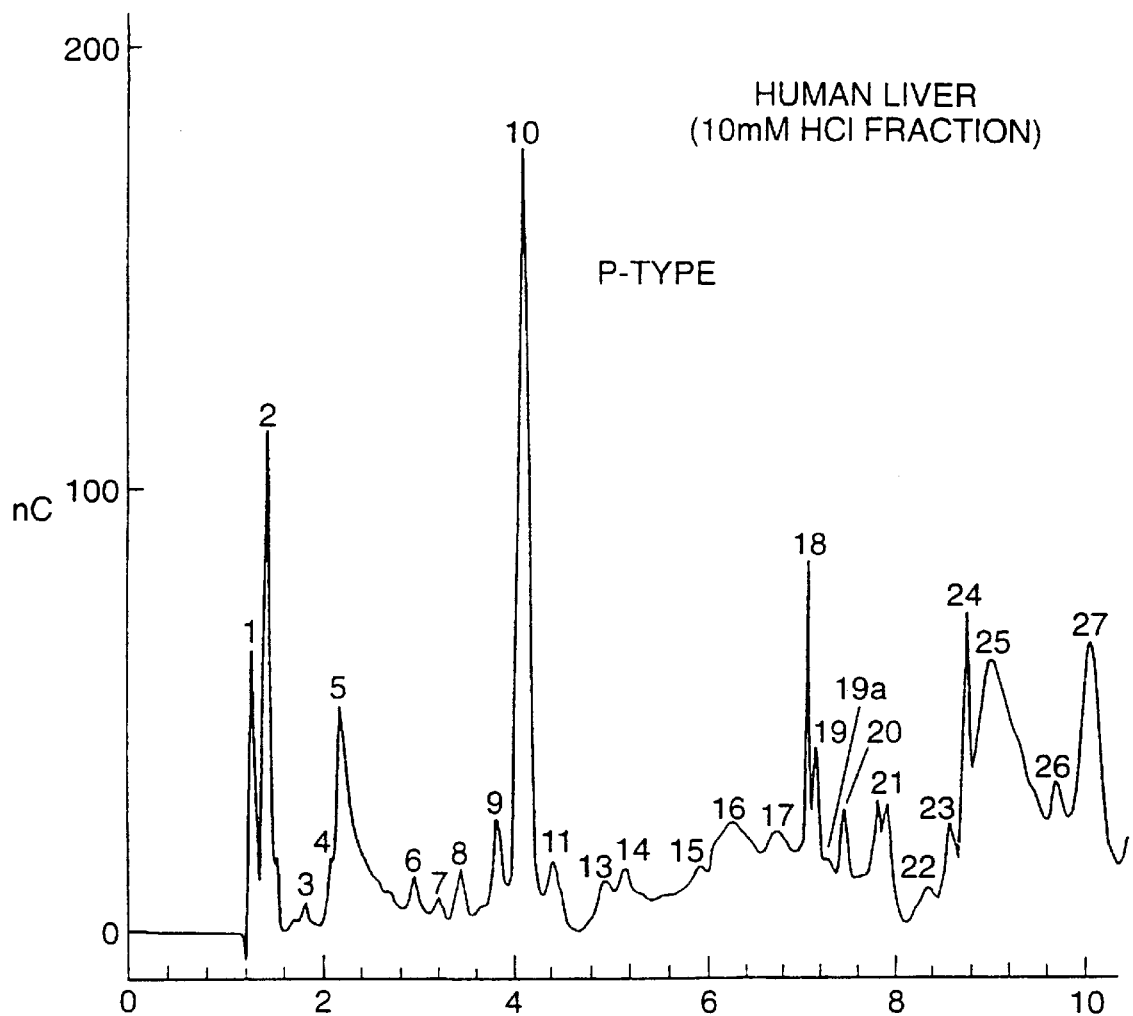
FIG. 1 shows DX500 HPLC of purified P-type family of IPG mediators from human liver.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. These parts of the compound constituting its active region are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

In the present case, it is expected that synthetic compounds containing all or part of the active substituents of the P-type IPG could be useful as therapeutics.

Antagonists

Antagonists to the P-type substances include substances which have one or more of the following properties:

(a) substances capable of inhibiting release of the P-type mediators;

(b) substances capable of reducing the levels of P-type mediators via a binding substance (e.g. an antibody or specific binding protein); and/or, (c) substances capable of reducing the effects of P-type mediators.

In one embodiment, the IPG antagonists are specific binding proteins. Naturally occurring specific binding proteins can be obtained by screening biological samples for proteins that bind to IPGs.

In a further embodiment, the antagonists are antibodies capable of specifically binding to P-type IPGs. The production of polyclonal and monoconal antibodies is well established in the art. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-239400. A hybridoma producing a monoclonal antibody may be subject to genetic mutation or other changes, which may or may not alter the binding specificity of antibodies produced.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al, Nature, 357:80–82, 1992). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanised antibodies in which CDRs from a non-human source are grafted onto human framework regions, typically with the alteration of some of the framework amino acid residues, to provide antibodies which are less immunogenic than the parent non-human antibodies, are also included within the present invention.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The antibodies described above may also be employed in the diagnostic aspects of the invention by tagging them with a label or reporter molecule which can directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are colored, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

In a further embodiment, the IPG antagonists are synthetic compounds. These may be produced by conventional chemical techniques or using combinatorial chemistry, and then screened for IPG antagonist activity. These compounds may be useful in themselves or may be used in the design of mimetics, providing candidate lead compounds for development as pharmaceuticals. Synthetic compounds might be desirable where they are comparatively easy to synthesize or where they have properties that make them suitable for administration as pharmaceuticals, e.g. antagonist which are peptides may be unsuitable active agents for oral compositions if they are degraded by proteases in the alimentary canal. Mimetic design, synthesis and testing is generally used to avoid randomly screening large number of molecules for a target property.

Pharmaceutical Compositions

The mediators and antagonists of the invention can be formulated in pharmaceutical compositions. These compositions may comprise, in addition to one or more of the mediators or antagonists, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the are are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whether it is a polypeptide, antibody, peptide, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980. In a preferred embodiment, dosage levels will be determined as producing euglycaemic conditions.

A composition may be administered alone or in combination with other treatments, either simultaneously or sequentially dependent upon the condition to be treated.

Diagnostic Methods

Methods for determining the concentration of analytes in biological samples from individuals are well known in the art and can be employed in the context of the present invention to determine the ratio of P- and A-type inositol-phosphoglycans (IPGs) in a biological sample from a patient. This in turn can allow a physician to determine if the ratio or level of P- and A-type IPGs is out of balance having regard to the patient and the condition being tested for. Examples of diagnostic methods are described in the experimental section below.

Preferred diagnostic methods rely on the determination of the ratio of P- and A-type IPGs. The methods can employ biological samples such as blood, serum, tissue samples or urine.

The assay methods for determining the concentration of P- and A-type IPGs typically employ binding agents having binding sites capable of specifically binding to one or more of the P- or A-type IPGs in preference to other molecules. Examples of binding agents include antibodies, receptors and other molecules capable of specifically binding the IPGs. Conveniently, the binding agent(s) are immobilised on solid support, e.g. at defined locations, to make them easy to manipulate during the assay.

The sample is generally contacted with the binding agent(s) under appropriate conditions so that P- and A-type IPGs present in the sample can bind to the binding agent(s). The fractional occupancy of the binding sites of the binding agent(s) can then be determined using a developing agent or agents. Typically, the developing agents are labelled (e.g. with radioactive, fluorescent or enzyme labels) so that they can be detected using techniques well known in the art. Thus, radioactive labels can be detected using a scintillation counter or other radiation counting device, fluorescent labels using a laser and confocal microscope, and enzyme labels by the action of an enzyme label on a substrate, typically to produce a colour change. The developing agent(s) can be used in a competitive method in which the developing agent competes with the analyte for occupied binding sites of the binding agent, or non-competitive method, in which the labelled developing agent binds analyte bound by the binding agent or to occupied binding sites. Both methods provide an indication of the number of the binding sites occupied by the analyte, and hence the concentration of the analyte in the sample, e.g. by comparison with standards obtained using samples containing known concentrations of the analyte. In preferred embodiments, this can then be used to determine the P:A type ratio.

Methods

Isolation and characterisation of inositol phosphoglycans

Inositolphosphoglycans (IPG) were purified as follows from frozen human liver. The frozen tissue (90 g) was powdered under liquid nitrogen and placed directly into boiling 50 mM formic acid containing 1 mM EDTA and 1 mM 2-mercaptoethanol (3 mL of buffer per gram (wet weight) of tissue). After 1 min homogenisation with a polytron mixer (Kinematica, Littau, Switzerland), the solution was further boiled for 5 min. The solution was then cooled on ice and centrifuged at 29,500 g for 2 h at 4° C. The supernatant was treated with 10 mg/mL activated charcoal for 30 min with stirring at 4° C. The charcoal suspension was centrifuged at 29,500 g for 1 h at 4° C. and the clear supernatant recovered. The solution was then diluted ten-fold with distilled water, adjusted to pH 6.0 with 10% $NH_4OH$ solution and then gently shaken overnight at room temperature with AG1-X8 (formate form) resin (0.3 mL resin per mL solution). The resin was then poured into a chromatography column (2.5×60 cm) and washed sequentially with water (2 bed volumes) and 1 mM HCl (2 bed volumes). Then, the material was eluted with 10 mM HCl (5 bed volumes) to obtain an IPG P-type fraction. This fraction was adjusted to pH 4.0 with 10% $NH_4OH$ solution and then dried in a rotary evaporator. The dried material was redissolved in distilled water, lyophilised twice and divided into five aliquots for both chemical and biochemical analyses. For analyses, aliquots of each type of preparation were dissolved in 200 µL of Hanks Medium and adjusted to pH 7.0 with 1 M KOH. The mediators extracted from the equivalent of 16 g (wet weight) of tissue were dissolved in a final volume of 200 µL (stock solution). Therefore, 10 µL of stock represents the amount of the P-type mediator recovered from 800 mg of starting tissue.

Pronase treatment

IPG was treated with Pronase E as described elsewhere. Briefly, a stock solution of the enzyme (10 mg/mL) was preincubated at 60° C. for 30 min in 100 mM Tris-HCl buffer, pH 8.0, to inactivate contaminating enzymes which may be present. Digestion of the sample was started by addition of pronase solution (30 µL) to IPG samples in 200 µL of 100 mM Tris-HCl buffer at pH 7.8 at 37° C. After two hours, the reaction was terminated by boiling for 3 min and removed by acid precipitation.

IPG purification by paper chromatography

IPG was dissolved in a minimum amount of water and applied to a 3 MM chromatography paper (3×50 cm, origin at 8.5 cm). Descending paper chromatography was performed using n-butanol/ethanol/water (4:1:1, v/v/v) and the chromatogram was developed for 9 h. After drying, the paper was cut every centimeter (−1 to +35 cm from the origin) and the material associated the fraction eluted with water (60 µL, 5 washes). The fraction was evaporated to dryness and redissolved either in water or in Hanks solution (60 µL) and neutralized with 1 N KOH prior to the determination of free amino groups, phosphate content or to assay biological activities.

High voltage paper electrophoresis

The material eluted from fractions 1 to 6 after paper chromatography, was pooled, redissolved in a small volume of water and applied to a 3 MM electrophoresis paper. Bromophenol blue and tritiated inositol phosphates mixture were added as standards. The samples were electrophoresed for 30 min at 80 Vcm$^{-1}$ in pyridine/acetic acid/water (3:1:387, v/v/v), pH 5.4. Neutral compounds remained at the point of application, while negatively charged compounds moved towards the anode. After the paper was dried, fractions were cut out every one cm and eluted with water.

Vydac HPLC chromatography

This technique was used to isolate and purify individual fractions containing the mediators. The P-type IPG was applied to a Vydac 301 PLX575 HPLC column. The column was eluted as follows:

Solvent:

Ammonium acetate 500 mM pH 5.5,

Gradient conditions:

0–5% over 12 minutes,

5–21% over the next 13 minutes,

21–80% over 25 minutes,

80–100% over 5 minutes.

The fractions were then assayed for phosphate and growth promoting activity using EGF-transfected fibroblasts.

Determination of free amino groups

Measurement of free amino groups was performed as described below. Samples and standards (0–100 nmol of D-(+)-glucosamine hydrochloride, Sigma) were dissolved in ultrapure water (50 µL) before sequentially adding sodium borate (0.14 M, pH 9) and fluorescamine (0.75 mg/ml prepared in dry acetone). Emission fluorescence at 475 nm was observed after excitation at 390 nm using a spectrofluorimeter.

Determination of phosphate content

Total phosphate levels were assayed as described below. Samples and standards (0–100 nmoles of $Na_2HPO_4$) were evaporated to dryness and hydrolysed with perchloric acid (70%) at 180° C. for 30 min. After cooling to room temperature, ultrapure water (250 µL), $(NH_4)_2MoO_4$ (100 µL of a 2.5% solution) and ascorbic acid (100 µl of a 10% solution) were sequentially added. Colour development was achieved by heating the samples at 95° C. for 15 min. Optical absorbance was measured at 655 nm in a microplate reader.

Interaction of IPG with Ion Exchange resins and Sep-Pak C18 cartridges

Thirty microliters of stock solution (see above) were loaded onto columns containing 600 µL of either AG3-X4 (HO$^-$), AG50-X12 (H$^+$) or onto Sep Pack C18 cartridges and then eluted with water (5 bed volumes). The solutions were concentrated to dryness and the residues obtained redissolved in 30 µL of Hanks and adjusted to pH 7.0.

Evaluation of cAMP-dependent protein kinase activity

The ability of the IPG fraction to inhibit the activity of the cyclic AMP-dependent protein kinase was assessed by using histone IIA as substrate. The reaction mixture (100 µL) contained 25 mM HEPES buffer (pH 7.6), 10 µM MgATP (10$^6$ cpm [γ-$^{32}$P]ATP), histone IIA (50 µg protein), and catalytic subunit of PKA (60 units/mL). In all the determinations, 10 µL of IPG solution (see above) was added to the reaction mixture. After incubation at 37° C. for 10 min, the reaction was stopped and proteins precipitated with 10% trichloroacetic acid (100 µL) and 2% bovine serum albumin (10 µL) and the incorporation of $^{32}$P into proteins was determined.

Evaluation of the pyruvate dehydrogenase phosphatase (PDH) activity

Pyruvate dehydrogenase complex (PDC) and the PDH phosphatase were prepared and stored at −80° C. until use. The assay for both PDH phosphatases, in the presence or absence of insulin mediator, was based upon the initial rate of activation of inactivated, phosphorylated PDH complex. The initial activity of the PDC was 8–13 units/ml (1 unit of enzyme produces 1 µmol NADH/min) and after inactivation with ATP, 0.3–0.5 units/ml (inactivated PDC). A two stage assay was used to quantitate the phosphatase activity. A sample of inactivated PDC (50 µL) was preincubated at 30° C. with 1 mg/mL fat-free BSA, 10 mM $MgCl_2$, 0.1 mM $CaCl_2$ and 1 mM DTT in 20 mM potassium phosphate buffer at pH 7.0 (total volume 250 µL) for three minutes. At this time, 10 µL of the PDH phosphatase and 10 µL of IPG were added and the incubation continued for a further 2 min. At the end of this time, 200 µL of the mix was removed and added to 100 µL of 300 mM NaF. The activated PDH was determined at the second stage photometrically by measuring the rate of production of NADH. One hundred microliters of the stopped reaction were added to 1 mL of reaction mixture containing 50 mM potassium phosphate buffer at pH 8.0, 2.5 mM β-NAD$^+$, 0.2 mM TPP, 0.13 mM coenzyme A, 0.32 mM DTT and 2 mM sodium pyruvate. The production of NADH was followed at 340 nm for 5 min.

Evaluation of glycogen synthase activity

Glycogen synthase activity was assayed as follows. Fat cells were prepared from epididymal adipose tissue using 140–150 g rats (Wistar strain). Fat pads from 3 rats were cut into small pieces and incubated in 8 ml of Krebs ringer bicarbonate containing 2% albumin plus 24 mg of collagenase for 25 minutes at 37° C. The isolated cells were filtered and washed in 3×10 ml Krebs ringer phosphate medium containing 30 mg/ml of bovine serum albumin (Fraction v, Sigma), the pH was adjusted to 7.4 with NaOH after addition of ablumin. The washed cells were also resuspended in Krebs ringer phosphate (10 ml of medium/g of original tissue).

For measurement of enzyme activities, three incubation vessels were set up, each contained 5 ml cells. These were no additions to the first, the second contained 20 µl insulin (25 mU/ml) and the third 10 µl placenta IPG. Incubation was for 5 min in air. The tubes were then spun at 1500 rpm for 30 seconds and the supranatant discarded.

The reaction was stopped with 0.5 ml cold buffer (100 mM KF/10 mM EDTA/1 mM benzamidine (4), pH 7.0) and the cells homogenized and transferred to Eppendorf tubes. These were spun at 10,000 g for 15 min and the middle layer collected for enzyme assay. All tubes were set up in duplicate and measured in the presence of 0.01 mM glucose 6-phosphate except the maximally activated glycogen synthase tube which contained 7.2 mM glucose 6-phosphate. Samples (30 µl) were added to 60 µl of a solution containing 50 mM tris buffer (pH 7.8), 20 mM EDTA, 25 mM KF, 10 mg/ml of glycogen, and 6.7 mM UPD-[U-$^{14}$C] glucose (approximately 200,000 cpm) and then incubated at 30° C. for 15 min. Glycogen synthase activity is expressed as a percentage of the total synthase activity (G6P maximum).

Measurement of cellular proliferation in fibroblasts

EGFRT17 fibroblasts were routinely grown in Dulbecco's Modified Eagle's Medium (DMEM) containing 10% v/v foetal calf serum, 2 mM L-glutamine, 100 units/mL penicillin and 100 μg/mL streptomycin at 37° C. in a humidified atmosphere of 5% $CO_2$. The cells were subcultured when they approached 80% confluence. The EGFRT17 cells are NIH 3T3 fibroblasts transfected with the human epidermal growth factor receptor [32,35]. To evaluate fibroblast cell proliferation, cells were plated into 96-well microtiter wells at a density of $10^4$ cell per well in DMEM containing 10% FCS. After 24 h the medium was removed, the cells washed twice with Hanks medium, serum free medium was added, and the cells were incubated for a further 24 h period. At this point the cells were stimulated with serum, IPG preparations or the appropriate controls. Eighteen hours later [$^3$H] thymidine (1 μCi/well) was added to each well for 4 h. At the end of this treatment, the cells were washed twice with Hanks solution, trypsinised, and radioactivity associated with cellular DNA determined using a cell harvester. For the cell proliferation assays, the dilutions are final dilutions. For example, 2.5 μL of the stock solution is added to a final volume of 100 μL, or 1/40 dilution.

Protocol for sandwich ELISA

The protocol below sets out an indirect, non-competitive, solid-phase enzyme immunoassay (sandwich ELISA) for the quantification of inositolphosphoglycans (IPG) in biological fluids, such as human serum.

In the assay, monoclonal IgM antibodies are immobilised on a solid phase. Tissue culture supernatant, ascitic fluid from mice with a peritoneal tumour induced by injecting hybridoma cells into the peritoneum and purified monoclonal antibody have been used in the immunoassay. F96 Maxisorp Nunc-Immuno plates were used for these assays. Maxisorp surface is recommended where proteins, specially glycoproteins such as antibodies, are bound to the plastic.

The immobilised antibody captures the antigen from the test sample (human serum of IPG used like a positive control).

A bridging antibody (a purified polyclonal IPG antibody from rabbit) is needed to link the anti-antibody biotinylated to the antigen.

The detection method employs an anti-rabbit Ig, biotinylated species-specific whole antibody (from donkey) and a streptavidin-biotinylated horseradish peroxidase complex (Amersham), ABTS and buffer for ABTS (Boehringer Mannheim).

The ELISA assay can be carried out as follows:

1. Add 100 μl/well in all the steps.
2. Add monoclonal antibody diluted 1:100 in PBS in a F96 Maxisorp Nunc-Immuno plate. Incubate at least 2 days at 4° C.
3. Wash with PBS three times.
4. Add a blocking reagent for ELISA (Boehringer Mannheim) in distilled water (1:9) 2 hours at room temperature.
5. Wash with PBS-Tween 20 (0.1%) three times.
6. Add a purified polyclonal antibody (diluted 1:100 in PBS), overnight at 4° C.
7. Wash with PBS-Tween 20 (0.1%) three times.
8. Add an anti-rabbit Ig, biotinylated species-specific whole antibody (from donkey) (Amersham) diluted 1:1000 in PBS, 1 h 30 min at room temperature.
9. Wash with PBS-Tween 20 (0.1%) three times.
10. Add a streptavidin-biotinylated horseradish peroxidase complex (Amersham) diluted 1:500 in PBS, 1 h 30 min at room temperature.
11. Wash with PBS three times.
12. Add 2.2-Azino-di-(3-ethylbenzthiazoline sulfonate (6)) diammonium salt crystals (ABTS) (Boehringer Mannheim) to buffer for ABTS (BM): Buffer for ABTS is added to distilled water (1:9 v/v). 1 mg of ABTS is added to 1 ml of diluted buffer for ABTS.
13. Read the absorbance in a Multiscan Plus P 2.01 using a 405 mm filter in 5–15 min.

Results

IPG isolation and biological activities

IPGs were extracted from human liver and placenta as follows. Briefly, the extract was prepared by heat and acid treatment of a tissue homogenate, processed from tissue immediately frozen in liquid nitrogen after removal from the patient, therefore preventing the action of phosphatases. After centrifugation and charcoal treatment, the solution was allowed to interact overnight with an anion exchange resin (AG1-X8, formate form). The resin was washed sequentially with water and dilute hydrochloric acid. Elution with 10 mM HCl produced a P-type IPG fraction which was active in stimulating pyruvate dehydrogenase phosphatase and glycogen synthesis and stimulated proliferation of EGF receptor transfected fibroblasts. This fraction was then subjected to descending paper chromatography using 4/1/1 butanol/ethanol/water as solvent, followed by purification using high-voltage paper electrophoresis in pyridine/acetic acid/water, and finally purification using Dionex (trade mark) anion exchange chromatography. FIG. 1 shows a sharp spike (fraction no. 10) representing the major P-type substance.

Metal analysis

Metal ion analysis was performed on a DX500 system with visible detection at 520 nm.

The separation was achieved using IonPac mixed bed ion exchange columns with pyridine-2,6-dicarboxylic acid eluent and post column reaction with pyridial azo resourcinol.

The P-type samples (P1 and P2) were reconstituted in 100 μl of water. 10 μl of this solution was taken, 10 μl of conc HCl added and the sample left overnight. Then, 80 μl of water was added to the mixture and 10 μl of this solution was analysed. Blank HCl samples acted as controls.

|  | μg/ml Zn | μg/ml Mn | μg/ml Fe | Averages |
|---|---|---|---|---|
| P1 | | | | |
| #1 | 12.31 | 3.10 | 14.04 | 2.27 μg/ml Zn |
| #2 | 2.22 | 3.17 | 14.10 | 3.14 μg/ml Mn |
| | | | | 14.07 ∞g/ml Fe |
| P2 | | | | |
| #1 | 2.49 | 3.35 | 15.28 | 2.45 μg/ml Zn |
| #2 | 2.38 | 3.41 | 15.49 | 3.36 μg/ml Mn |
| #3 | 2.47 | 3.33 | 15.10 | 15.29 μg/ml Fe |
| Blank | | | | |
| #1 | — | — | 10.24 | |
| #2 | — | — | 10.26 | 10.28 μg/ml Fe |
| #3 | — | — | 10.33 | |
| Blank | | | | |
| #1 | — | — | 8.42 | 8.32 μg/ml Fe |
| #2 | — | — | 8.21 | |

Average of Blank 1 and 2 = 9.2 μg/ml Fe

This shows for the first time that the P-type IPG isolated from human liver contains $Mn^{2+}$ and/or $Zn^{2+}$ ion.

Inhibition of cAMP dependent protein kinase

The ability of the IPG to inhibit cAMP-dependent protein kinase was tested by determining the incorporation of $^{32}P$ into washed histone IIA. The addition of the P-type IPG fraction diluted 1/10, caused 57.7±16.4 (n=4) percent inhibition of the kinase activity. While this effect was dose dependent, the P-type IPG did not give significant inhibition of kinase activity. These experiments are in agreement with our previous data for rat-derived IPGs. In contrast to the P-type IPG fraction, the A-type fraction we have described elsewhere contains the predominant inhibitor activity against cAMP dependent protein kinase.

Stimulation of PDH phosphatase

Figure 6:
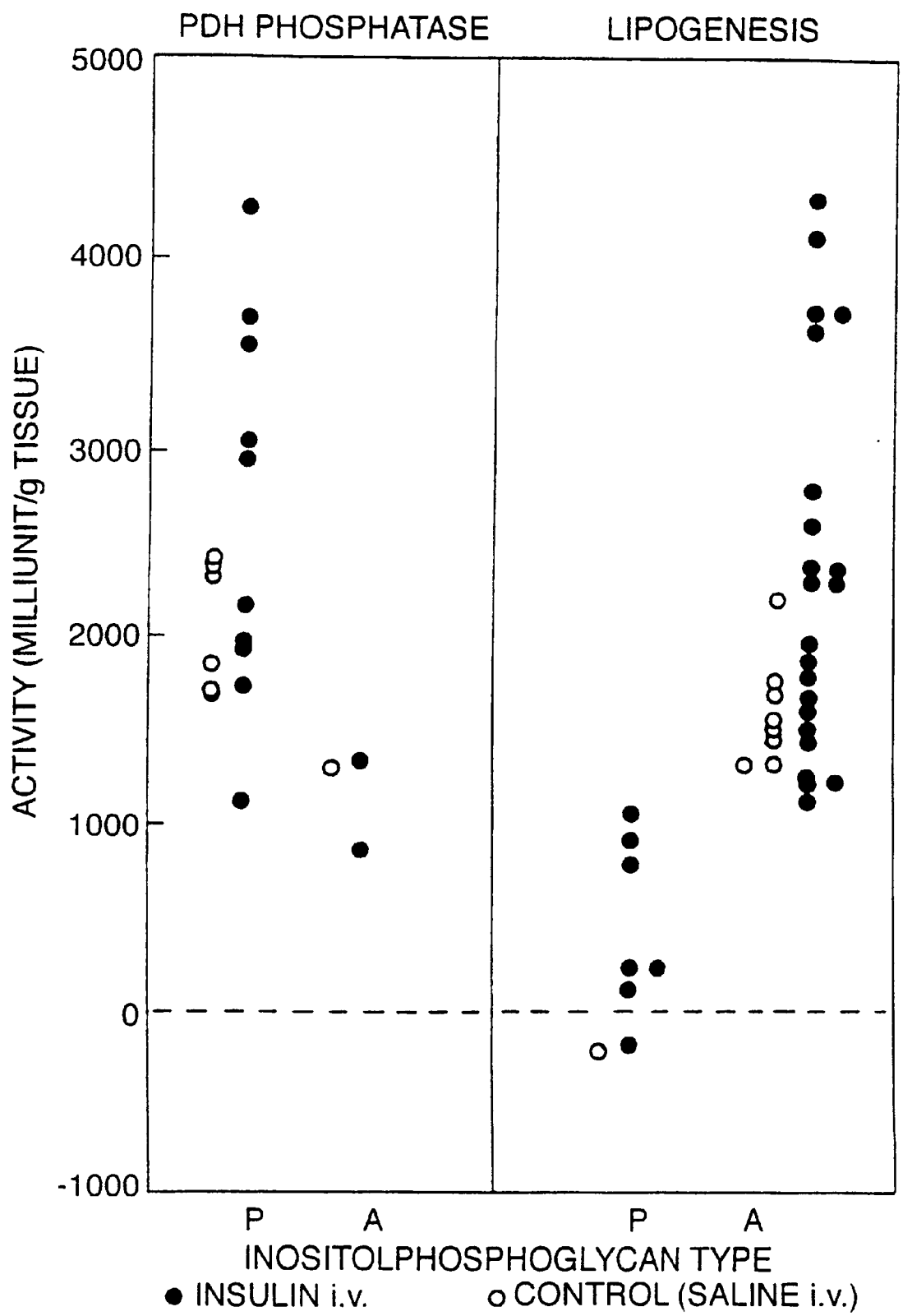
FIG. 6 shows the quantitative increase in IPG release following infusion with insulin.

The ability of the P-type IPG fraction to stimulate pyruvate dehydrogenase phosphatase isolated from bovine heart was determined. Table 1 shows that both human livers contained substantial PDH phosphatase stimulating activity in the P-type eluate. The amount of activity recovered was similar to that recovered from rat liver in the absence of insulin stimulation (see Table 1). Insulin stimulation of rat liver results in a two-fold increase in activity 2 minutes after insulin infusion (see FIG. 6). We have previously used the nomenclature P-type to denote the IPG family of compounds present in the 10 mM fraction, to highlight this activity.

IPG can substitute for $Mn^{2+}$ in vitro

The P-type insulin IPG can completely substitute for manganese in the activation of a variety of Mn-dependent enzymes including pyruvate dehydrogenase phosphatase. Free manganese in the absence of calcium is not able to activate the enzyme (see below line 6 compared to line 2). However, the IPG Mn co-factor is able to stimulate activity in the absence of calcium (see line 4). The effect of co-factor binding is to make the PDH phosphatase responsive to calcium (see line 3). Release of the IPG therefore activates the PDH phosphatase and the enzyme is now primed for further activation in the event calcium is also released intracellularly. In a homogolous fashion calcium is able to activate to PDH phosphatase (line 1) and the enzyme is now primed to respond to the release of IPG (line 3).

| PDH phosphatase | (activity) |
|---|---|
| $+Mg^{2+}$ $+Ca^{2+}$ | Δ 0.334 OD/min (1) |
| $+Mg^{2+}Ca^{2+}$ $+Mn^{2+(sat)}$ | Δ 0.680 OD/min (2) |
| $+Mg^{2+}$ $+Ca^{2+}$ $+IPG$ | Δ 0.833 OD/min (3) |
| $+Mg^{2+}$ $+IPG$ | Δ 0.130 OD/min (4) |
| $+Mg^{2+}$ | Δ 0.000 OD/min (5) |
| $+Mg^{2+}$ $+Mn^{2+(sat)}$ | Δ 0.000 OD/min (6) |

Glycogen synthase activity

The results below indicate that the $Mn^{2+}$ containing P-type IPGs stimulate glycogen synthase activity, in accordance with previous results carried out on uncharacterised fractions from rat tissues.

| Incubation | Stimulation as % of G6P Maximum |
|---|---|
| No additions, + 7.2 mM G6P | 100 |
| Insulin | 6.54 |
| Placenta P-type (1) | 2.82 |
| Placenta P-type (2) | 4.05 |

Placenta (1) was extracted using the equivalent of 5 g placenta and had been stored freeze-dried since tested before.
Placenta (2) was from the same extraction but was a mixture of 3 samples of the same day in which the amount of tissue was 2.5, 1.0 and 0.5 g but had been stored in solution at −20° C..

Effect on lipogenesis

The fraction containing the P-type IPG were added to rat adipocytes and the ability of this fraction to stimulate lipogenesis determined. Table 1 shows that no lipogenic activity was found in the P-type fraction from human liver.

Effects on NIH 3T3 fibroblast proliferation

The P-type IPG fraction was assayed for its ability to support proliferation of fibroblasts in the absence of serum. For rat tissue this assay has been used to estimate the relative abundance of the mediators since P-type mediators are active in the assay. The P-type fraction derived from human liver was found to be mitogenic when added to fibroblasts transfected with the EGF receptor in serum-free media. FIG. 2 shows the dose-dependent effect obtained for the fraction. Saturation was not yet obtained at the highest concentrations used. Both fractions however were able to induce proliferation at least 2–2.5 fold greater than 10% FCS alone.

Descending paper chromatography

A portion of the P-type material was treated with Pronase E for 2 hours and then the pronase removed by acid precipitation. The solution remaining was concentrated, redissolved in water and subjected to purification by descending paper chromatography using n-butanol/ethanol/water. After development for 9 hours, the presence of phosphate and free amino groups were detected. FIG. 3 shows the chromatogram profiles for the putative P-type mediator, following analysis for phosphate. Compounds containing phosphate were found to migrate between the origin and 5 cm. The paper chromatograms were also analysed for the presence of free amine groups as shown in FIGS. 3c and d. Again compounds containing free amino groups were present between the origin and a migration distance of 5 cm. Incubation with pronase made no difference to the migration of the compounds as assessed by the phosphate analysis as shown in FIGS. 3a and b.

Interaction with Ion Exchange resins and Sep-Pak C18 cartridges

The behaviour of IPG in its interaction with two different ion exchange resins and a reverse phase C18 column were determined by the ability of the eluates to induce thymidine incorporation into EGFTR17 DNA cells. The results are shown in Table 2. In the case of the reverse phase, 50–60% of the activity was recovered for the P-type IPG. These results demonstrate that the P-type mediator is either a mixture of hydrophilic and hydrophobic compounds both having proliferative activity, or the P-type mediators form some type of complex equilibria resulting in partitioning depending on the physical state. Table 2 also shows that the P-type mediators could not be recovered from either a cation exchange column (AG50-X12) or an anion exchange column (AG3-X4). This is consistent with the presence of dual functional groups such as free amino and phosphate moieties as was found in FIG. 3.

Activity requires metal ions

The IPGs were extracted with dithizone (see Appendix 1, section 2) to remove all metal ions. Following extraction, the P-type IPG was inactive in the PDH phosphatase assay.

IPG containing carbohydrates

Chromatograms of purified IPG P-type from human liver were detected by pulse-amperimetric detections (conditions given in Appendix 1, section 4).

The presence of various forms of inositol (myo-inositol, chiro-inositol, pinitol) was confirmed using a DX500 system and a Carbo Pac MA1 column and pulsed amperimetric detection (method given in Appendix 1, section 6).

Purification by high-voltage electrophoresis (HVE)

Figure 4A:
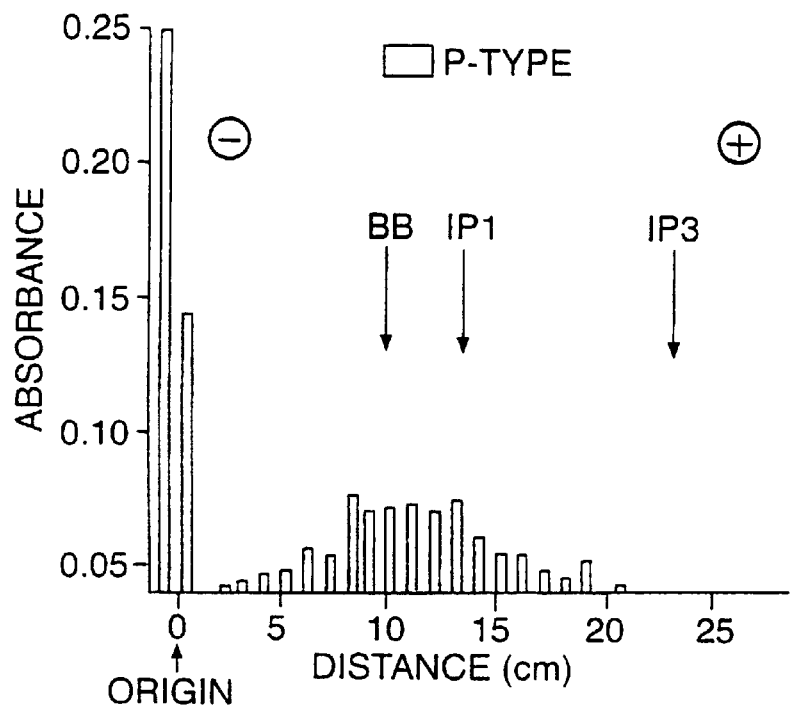
FIGS. 4a and 4b show the high voltage electrophoresis of IPG type-A and type-P modulators.
Figure 4B:
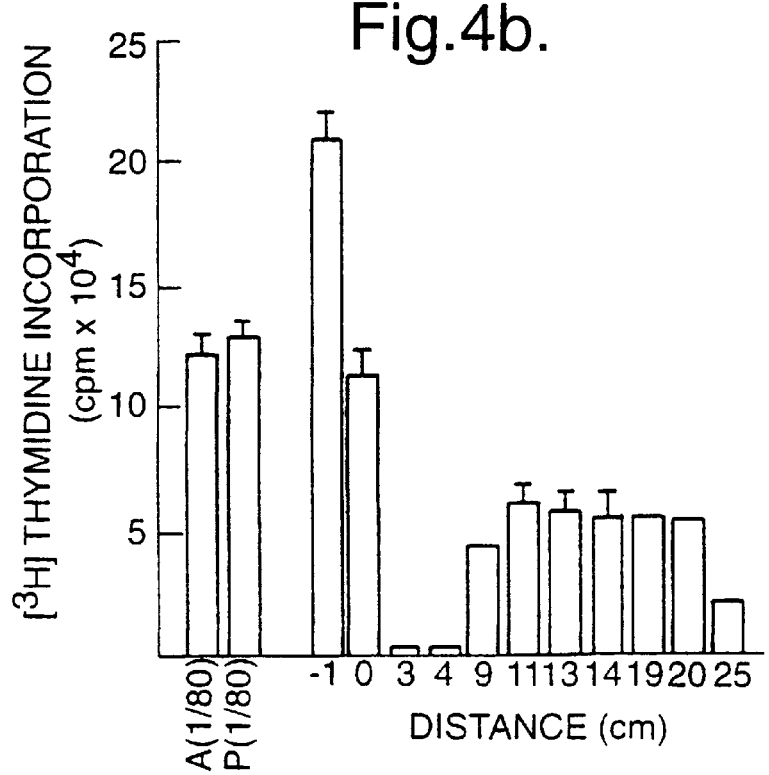

The material eluted from the paper after descending chromatography was subjected to high-voltage paper electrophoresis at pH 5.4. Under these conditions, negatively charged compounds containing phosphate, carboxy, or sulphate groups migrate towards the anode. A representative paper electrophoretogram of three independent experiments is shown in FIG. 4a following analysis for phosphate. Phosphate was detected at the origin and as a broad unresolved peak extending from 5 cm to 20 cm migration distance. The profiles for the P-type mediators were remarkably similar. The presence of phosphate at the origin indicates that compounds recovered in this position must have an equal number of positively charged moieties which neutralize the overall charge. Those compounds which migrate either have an excess of negatively charged groups (e.g. phosphate) over positively charged moieties (e.g. amino, metal). FIG. 4b demonstrates that the cell proliferation activity of the putative P-type mediator is still present after the pronase treatment, paper chromatography and HVE purification steps. The activity profile following HVE very closely mirrors the phosphate analysis shown in FIG. 4a with activity present at the origin and in a broad band extending to 20 cm migration distance. The fraction was then assayed for its ability to stimulate PDH phosphatase and this activity correlates very strongly (R=0.97) with the ability of the fraction to stimulate cell proliferation as shown in FIG. 5a. FIG. 5b demonstrates that there is a strong correlation (R=0.87) between the phosphate content of the putative P-type mediators isolated from the paper electrophoretogram and the ability of some of the fractions taken from the electrophoretogram to stimulate cell proliferation. The correlation between phosphate content and PDH phosphatase stimulating activity was also strong (R=0.73, data not shown).

The presence of hexoses and hexosamines was confirmed using a DX 500 system and a Carbo Pac PA1 column and pulsed amperimetric detection.

Vydac HPLC Chromatography

Figure 7:
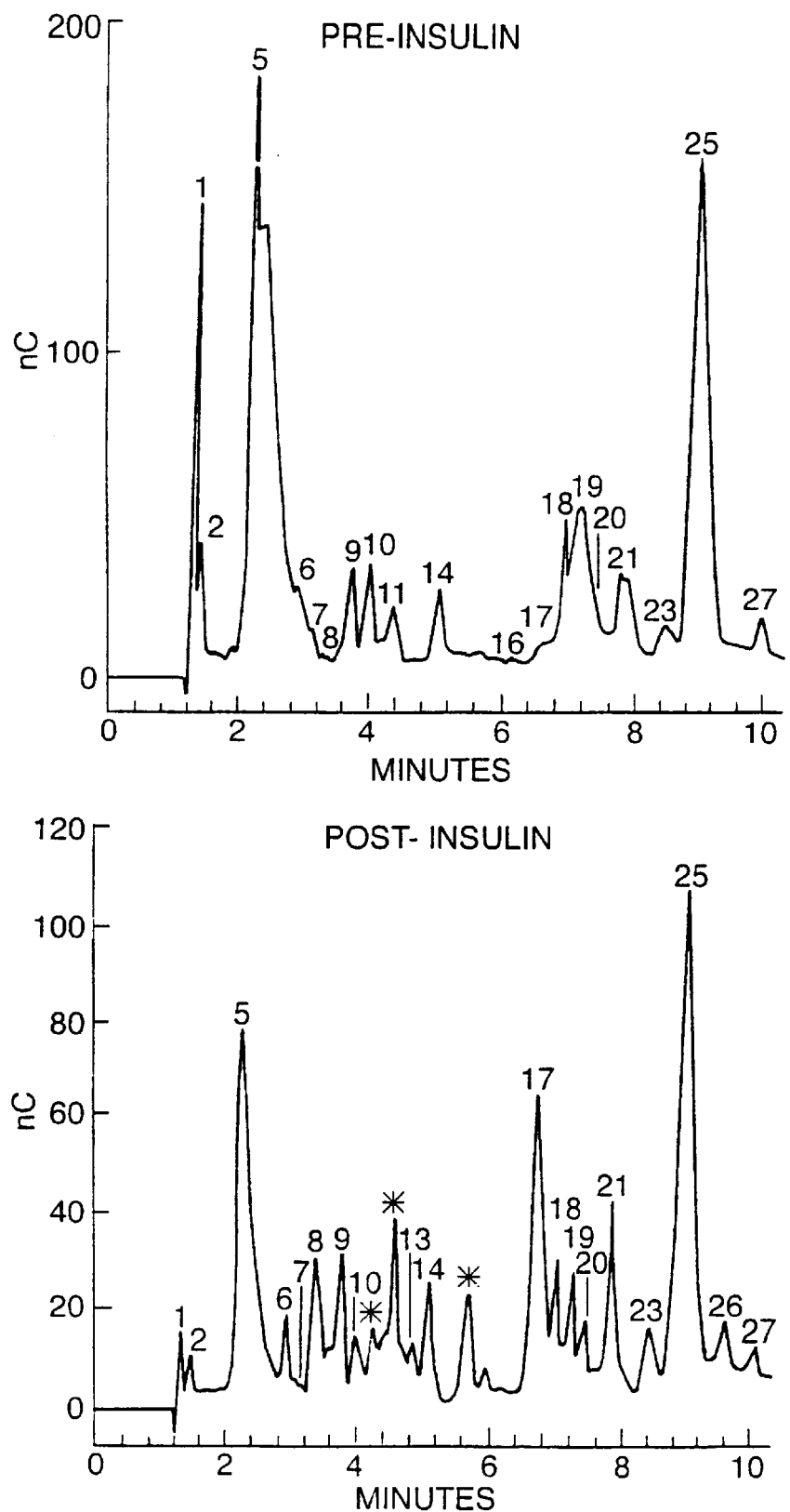
FIG. 7 the family of IPGs responsive to insulin as detected by DX500 anion exchange chromatography. Peaks with * are not present in the pre-insulin stimulated rat liver.
Figure 8:
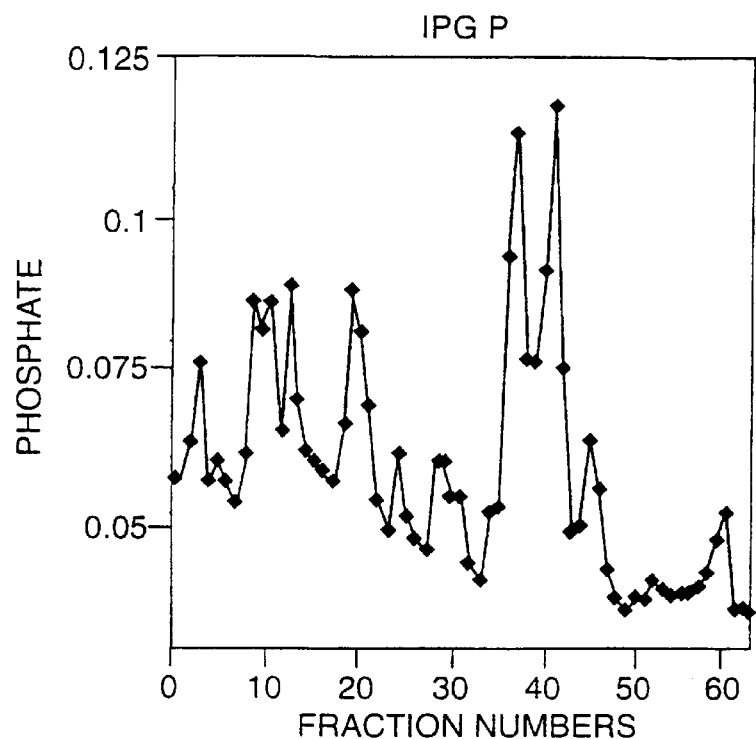
FIG. 8 shows the phosphate content of a family of P-type substances isolated and purified using Vydac HPLC chromatography.
Figure 9:
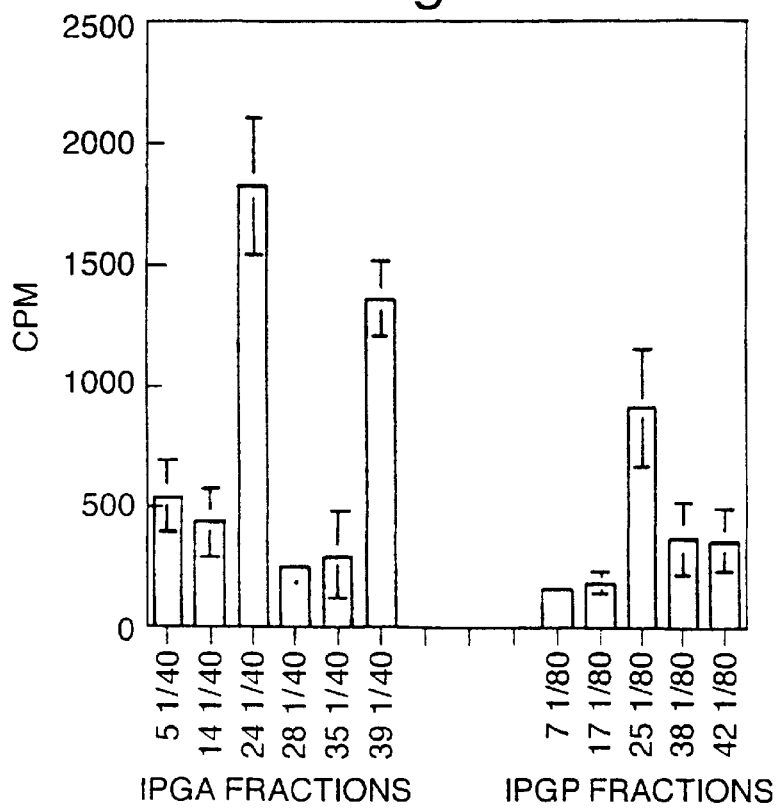
FIG. 9 shows the bioactivity of selected P-type substances isolated and purified using Vydac HPLC chromatography.
Figure 10:
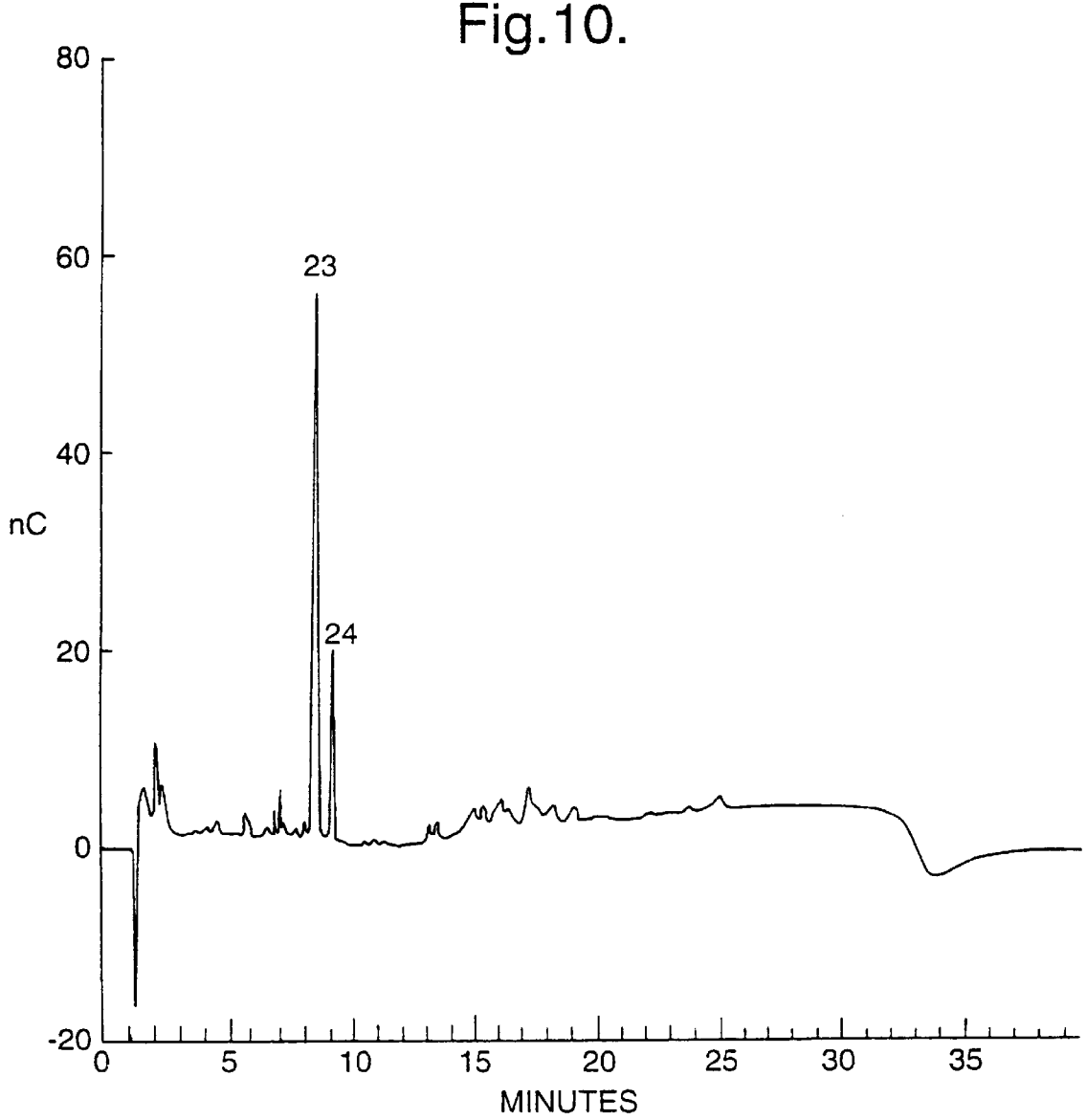
FIG. 10 shows the Dionex peak of a P-type fraction isolated using Vydac HPLC chromatography, showing that this fraction corresponds to peak 23 shown in FIGS. 1 and 7.

In order to demonstrate that it is possible to isolate and purify P-type mediators from samples containing the family of compounds shown in FIG. 1, fractions obtained from a Vydac 301 PLX575 HPLC column and were analysed for phosphate and growth promoting activity. FIG. 8 shows the phosphate levels of the different fractions and FIG. 9 shows the bioactivity of the selected fractions including 7, 17, 25, 38 and 42. The predominant growth promoting activity was found in fractions 23–25. The Dionex HPLC profile of the main active fraction is shown in FIG. 10. This fraction contains predominantly peak 23 shown in FIGS. 1 and 7.

Dithizone Treatment of Liver P-type

Three samples of liver P-type were used. All were suspended on day of use at the rate of 1 g liver in 10 μl water. All three preparations were tested before and after treatment with dithizone, while one preparation was also treated with Mn after dithizone to attempt to reactivate it. The reactivation procedure was to preincubate a de-metallized sample with 2.7 mM Mn for 15 min before it was added to the inactivated PDH mix.

| No | Treatment | Vol used | % stimulation | Units/g |
|---|---|---|---|---|
| 1. | Original P-1 | 5 μl | +58 | 2.32 |
| 2. | Treated P-1 | 5 μl | 0 | 0 |
| 3. | 2.7 mM Mn | 5 μl | −11 | 0 |
| 4. | Treated P-1 + 2.7 mM Mn | 5 μl | +30 | 1.20 |
| 5. | Original P-2 | 5 μl | +66 | 2.64 |
| 6. | Treated P-2 | 5 μl | +53 | 2.12 |
| 7. | P-2 extracted with chloroform | 5 μl | +91 | 3.64 |

-continued

| No | Treatment | Vol used | % stimulation | Units/g |
|---|---|---|---|---|
| 8. | Water extracted with chloroform | 5 μl | −2 | 0 |
| 9. | Original P-3 | 5 μl | +30 | 1.20 |
| 10. | Treated P-3 | 5 μl | +12 | 0.48 |

This experiment shows the following:
1. Treatment with dithizone decreased activity of all three specimens tried; P-1 by 100%, P-2 by 60% and P-3 by 20%.
2. Preincubation with Mn restored approx half activity.
3. Extraction of P-2 with chloroform alone enhances activity by almost 40%. This may imply the presence of a chloroform soluble inhibitor.
4. There is the anomaly that $10^{-4}$M Mn (assay no: 3 above) has no effect on P'ase activity, whereas previous results clearly show that this concentration has a marked stimulatory action on P'ase.

Thus, removal of metal removes all activity from the IPG, but this activity can be reconstituted.

Effect of Mn and Zn on the Reactivation of Dithizone Treated Liver P-type IPG

In the last experiment Mn only partially reactivated P-type IPG that had been stripped of its metal by treatment with dithizone. This might reflect that the IPG contains both Mn and Zn in the rough proportion of 3:2. The present experiment was to examine whether both metals activated and whether they were additive.

The P-1 sample used here was the same as that used in previous experiment although a second tube of that composite sample. The dithizone-treated sample was the same as that used previously. For reactivation, the de-metallized sample was pre-incubated for 15 mins with either 2.7 mM Mn, 1.8 mM Zn or 2.7 mM Mn-1.8 mM Zn. All samples tested on normal assay system using 10 μl P'ase and 5 ul of sample.

| No | Sample | % Stimulation |
|---|---|---|
| 1. | Original untreated P-1 | +43 |
| 2. | Treated P-1 | 0 |
| 3. | P'ase + 2.7 mm Mn | +12 |
| 4. | P'ase + 1.8 mM Zn | +122 |
| 5. | P'ase + Mn + Zn | +111 |
| 6. | Treated P-1 + Mn + Zn | +262 |

This experiment showed the following:
1. Z stimulated P'ase to a greater extent than did Mn.
2. The effect of Mn and Zn on P'ase was not additive.
3. The effect of the combined metals on inactivated IPG was to stimulate the inactivated IPG to a value appreciably greater than could be expected from the sum of the original activity+Mn+Zn (43+12+122=177) to a value of 262.

Thus, this experiment confirms that the P-type IPG may require a mixture of $Mn^{2+}$ and $Zn^{2+}$ for activity in some circumstances.

MALDI mass spectroscopy

Figure 11:
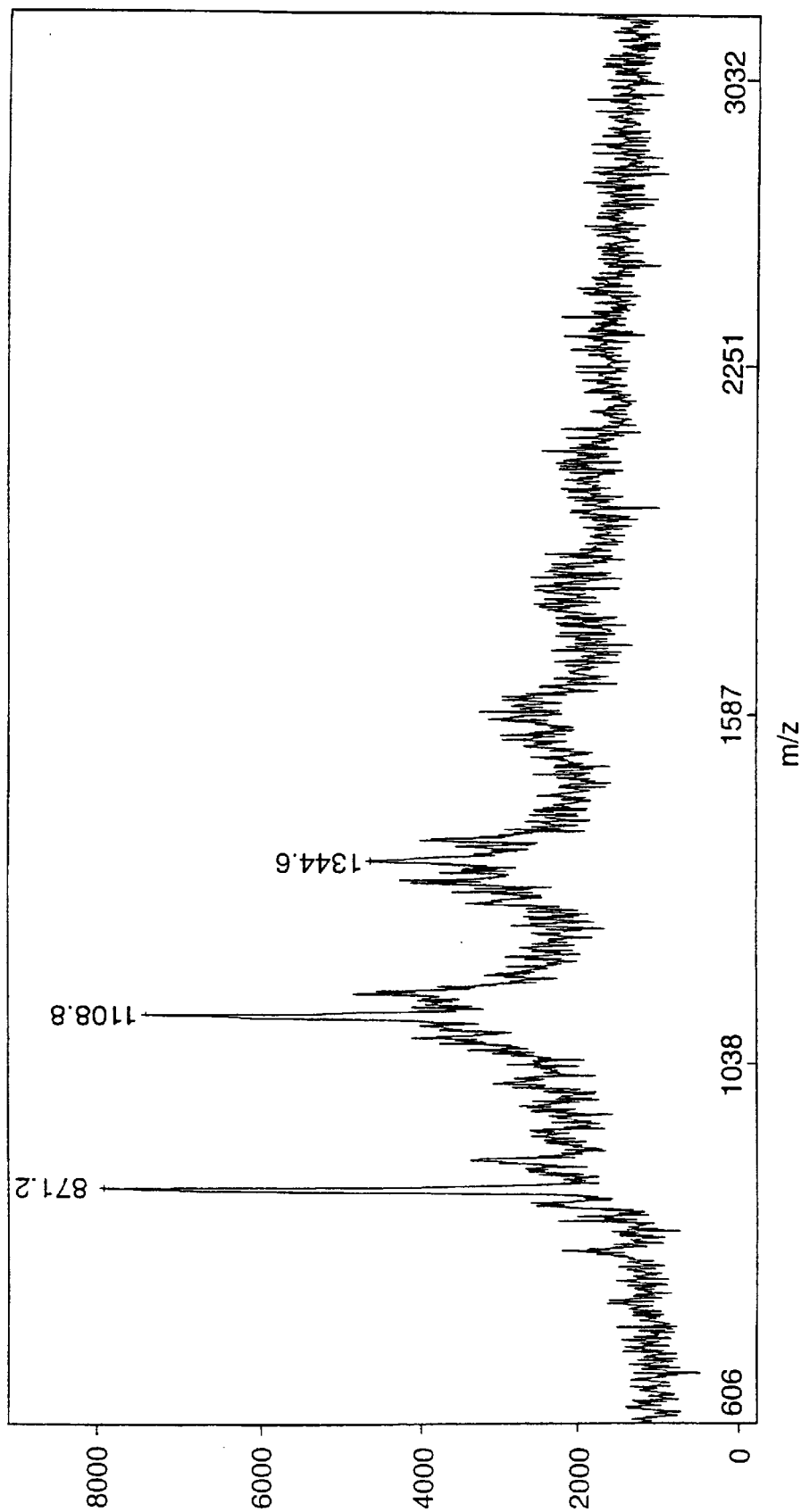
FIG. 11 shows a MALDI mass spectrum (negative mode) of a family of P-type IPGs.

High resolution MALDI mass spectrum (negative mode) of the family or P-type molecules is shown in FIG. 11. The family of structure are related by the addition of 236 or 237 m/z structure units, see the three marked peaks.

The molecular weights determined by negative mode MALDI mass spectroscopy differ from the actual molecular weights of the P-type substances by the removal of a $H^+$ atom, i.e. the actual weight can be obtained by adding +1 to the molecular weights of the peaks shown in FIG. 11. Thus, it is straightforward to determine the molecular weights based on the results in the figure.

Monoclonal antibodies

Inositolphosphoglycan (IPG) purified from rat liver by sequential thin layer chromatography (TLC) was used to immunise New Zealand rabbits and Balb/c mice by using conventional procedures.

After immunisation, monoclonal antibodies were prepared using the approach of fusion of mouse splenocytes ($5 \times 10^6$ cells/ml) with mutant myeloma cells ($10^6$ cells/ml). The myeloma cell lines used were those lacking hypoxanthine-guanine phopsphoribasyl transferase. The screening method of hybridoma cells was based on a non-competitive solid-phase enzyme immunoassay in which the antigen (IPG) was immobilised on a solid phase. Culture supernatants were added and positive hybridoma cells were selected.

A single cell cloning was made by limiting dilution. Hybridomas for three monoclonal antibodies (2D1, 5HG and 2P7) were selected. All monoclonal antibodies were determined to be IgM using a EK-5050 kit (Hyclone).

In order to test that all monoclonal antibodies recognised IPGs, a non-competitive solid-phase enzyme immunoassay was used. F96 Polysorp Nunc-Immuno Plates are used for the assay. The polysorp surface is recommended for assays where certain antigens are immobilised.

The immobilised antigen (IPG) diluted to 1:800 captured the monoclonal antibody from tissue culture supernatant, ascitic fluid, and when the purified monoclonal antibody was used.

The detection method used as anti-mouse IgM, biotinylated whole antibody (from goat) and a streptavidin-biotinylated horseradish peroxidase complex (Amersham), ABTS and buffer for ABTS (Boehringer Mannheim).

The same immunoassay was used to evaluate the polyclonal antibody. In this assay, the detection method employed an anti-rabbit Ig, biotinylated species—specific whole antibody (from donkey).

The antibodies can be purified using the following method. Fast Protein Liquid Chromatography (Pharmacia FPLC system) with a gradient programmer GP-250 Plus and high precision pump P-500 was used in order to purify a polyclonal IPG antibody.

A HiTrap protein A affinity column was used for purification of polyclonal IPG from rabbit serum. Protein quantitation was made using a Micro BCA protein assay reagent kit (Pierce).

Monoclonal IgM antibodies were purified in two steps. Ammonium sulfate precipitation was the method chosen as a first step. Tissue culture supernatant was treated with ammonium sulfate (50% saturation). Pellet diluted in PBS was transferred to dialysis tubing before the second step.

Since ammonium sulfate precipitation is not suitable for a single step purification, it was followed by gel filtration chromatography-antibody solution in PBS run into a Pharmacia Sepharose 4B column. Protein quantitation was made reading the absorbance at 220–280 nm in a Perkin-Elmer lambda 2 UV/VIS spectrophotometer.

Thus, this example shows that it is possible to raise monoclonal and polyclonal antisera to the A and P-type substances. These could be used as antagonists or binding agents.

DISCUSSION

Material isolated by elution from an AG1-X8 resin with 10 mM HCl (P-type IPG) stimulated pyruvate dehydrogenase phosphatase. This fraction also stimulated the proliferation of EGF-receptor transfected 3T3 cells and glycogen synthesis in adipocytes.

The biological characteristics of the P-type IPG fraction isolated from human liver were recovered after treatment with pronase, indicating that its activity is not due to either protein or peptides. The presence of phosphate and free amino groups suggests that these compounds could be similar to those reported to contain hexoses and hexosamines in their structure. The strong correlations between phosphate content and the ability of the mediators to stimulate cell proliferation (FIG. 5a) and PDH phosphatase stimulating activity (FIG. 5b) strongly suggests that phosphate is a key component of the putative mediators. The carbohydrate nature of these compounds is supported by their behaviour in descending paper chromatography, characteristic of carbohydrate-containing compounds and resembling that of the IPG isolated from insulin stimulated rat tissues. The Dionex profiles confirm the presence of carbohydrate. All experiments were consistent with the presence of P-type insulin-mimetic inositolphosphoglycans in the 10 mM fraction eluted from the anion exchange resin.

In humans, post-receptor tissue insulin resistance of glucose metabolism is a feature of non-insulin-dependent diabetes mellitus (NIDDM) and many other disorders. Resistance could result from an intrinsic defect in insulin signalling pathways or could be caused by the presence of a circulating inhibitor of insulin action or both. Defects in IPG-associated mediator pathways therefore are key targets for investigations on the pathogenesis of NIDDM.

The importance of IPG in insulin signalling comes from both in vitro and in vivo data. For example, mutant cells unable to make IPG respond to insulin by tyrosine phosphorylation, but without metabolic effects [1] and cells bearing kinase-deficient insulin receptors do not hydrolyse GPI following insulin stimulation [2]. There is also a correlation with insulin receptor level with both insulin action and breakdown of GPI [3]. The insulin resistance of cells from diabetic GK rats, which have a defect in GPI synthesis and release, can be overcome with IPG from bovine liver [4]. Similarly antibody to an enzymatically and chemically modified inositol phosphate glycan isolated from *Trypanosome brucei* blocks the effects of insulin [5,6,7,8] There is impairment of insulin-stimulated hydrolysis of GPI in adipocytes from streptozotocin-diabetic rats and impaired insulin activation of pyruvate dehydrogenase (PDH) and glucose utilisation [5].

PDH activity of NZO mice is unresponsive to insulin stimulation in the presence of significant stimulation of glucose transport and utilisation, suggesting a post-receptor defect at the level of insulin stimulation of this enzyme. Insulin stimulates the production of P-type mediators (activates PDH) in lean NZC mouse adipocytes but paradoxically causes a decrease in mediator production or activity in adipocytes of NZO mice [9]. No insulin antagonists are found. These results demonstrate in NZO mice a post-receptor defect of insulin action at the level of pyruvate dehydrogenase activation (i.e. P-type mediator). A defective mediator (or response to the mediator) has also been reported in adipocytes of insulin-resistant, type II diabetic Goto-Kakizaki rats [10] The decreased urinary chiro-inositol (hydrolysis product of P-type mediator) secretion found in patients with type II diabetes [11,12] suggests a similar post-receptor defect in human patients, although not all studies have been able to confirm these observations [13].

There is decreased urinary chiro-inositol in spontaneously diabetic (fat) rhesus monkeys [14], and chiro-inositol lowers plasma glucose in such monkeys and in streptozotocin-treated rats, and activates glycogen synthase [15]. Intravenous infusion of the mediators in streptozotocin-treated rats decreases plasma glucose without a change in the serum insulin concentrations and ip injection results in glycogenic changes in diaphragm.

REFERENCES

The contents of all of the references listed below or mentioned in the description above are incorporated herein by reference.

1. Lazar-D F, Knez J J, Medof-M E, Cuatrecasas-P, Saltiel-A R. 1994 Stimulation of glycogen synthesis by insulin in human erythroleukemia cells requires the synthesis of glycosyl-phosphatidylinositol. Proc Natl Acad Sci USA. 91: 9665–9669.

2. Villalba M, Alvarez J F, Russell D S, Mato J M, Rosen, O M. 1990 Hydrolysis of glycosyl-phosphatidylinositol in response to insulin is reduced in cells bearing kinase-deficient insulin receptors. Growth Factors. 2: 91–97.

3. Macaulay S L, Clark S, Larkins R G. 1992 Correlation of insulin receptor level with both insulin action and breakdown of a potential insulin mediator precursor: studies in CHO cell-lines transfected with insulin receptor cDNA. Biochim Biphys Acta. 1134: 53–60.

4. Farese R V, Standaert M L, Yamada K, Huang L C, Zhang C, Cooper D R, Wang Z, Yang Y, Suzuki S, Toyota T, Larner J. 1994 Insulin-induced activation of glycerol-3-phosphate acyltransferase by a chiro-inositol-containing insulin mediator is defective in adipocytes of insulin-resistant, type II diabetic, Goto-Kakizaki rats. Proc Natl Acad Sci USA. 91: 11040–11044.

5. Huang L C, Fonteles M C, Houston D E, Zhang C, Larner J. 1993 Chiroinositol deficiency and insulin resistance. III. Acute glycogenic and hypoglycemic effects of two inositol phosphoglycan insulin mediators in normal and streptozotocin-diabetic rats in vivo. Endocrinology. 132: 652–657.

6. Nestler, J E, Romero G, Huang L C, Zhang C G, Larner J. 1991 Insulin mediators are the signal transduction system responsible for insulin's actions on human placental steroidogenesis. Endocrinology. 129: 2951–2956.

7. Romero G, Gamez G, Huang L C, Lilley K, Luttrell L. 1990 Anti-inositolgylcan antibodies selectively block some of the actions of insulin in intact BC3H1 cells. Proc Natl Acad Sci USA. 87: 1476–1480.

8. Represa J, Avila M A, Miner C, Giraldez F, Romero G, Clemente R, Mato J M, Varela-Nieto I. 1991 Glycosyl-phosphatidylinositol/inositol Phosphoglycan: a signaling system for the low-affinity nerve growth factor receptor. Proc Natl Acad Sci USA. 88: 8016–8019.

9. Macaulay S L, Larkins R G. 1988 Impaired insulin action in adipocytes of New Zealand obese mice: a role for postbinding defects in pyruvate dehydrogenase and insulin mediator activity. Metabolism. 37: 958–965.

10. Farese R V, Standaert M L, Yamada K, Huang L C, Zhang C, Cooper D R, Wang Z, Yang Y, Suzuki S, Toyota T, et al. 1994 Insulin induced activation of glycerol-3-phosphate acyltransferase by a chiro-inositol-containing insulin mediator is defective in adipocytes of insulin-resistant, type II diabetic, Goto-Kakizaki rats. Proc. Natl, Acad. Sci. U.S.A. 91: 11040–4.

11. Kennington A S, Hill C R, Craig J, Bogardus C, Raz I, Ortmeyer H K, Hansen B C, Romero G, Larner J. 1990 Low urinary chiro-inositol excretion in non-insulin-dependent diabetes mellitus. N Engl J Med 323: 373–378.

12. Suzuki S, Kawasaki, H, Satoh Y, Ohtomo M, Hirai M, Harai A, Hirai S, Onoda M, Matsumoto M, Hinokio Y, et al. 1994 Urinary chiro-inositol excretion is an index marker of insulin sensitivity in Japanese type II diabetes. Diabetes-Care. 1994 17: 1465–8.

13. Ostlund R E Jr, McGill J B, Herskowitz I, Kipnis D M, Santiago, J V, Sherman W R. 1993 D-chiro-inositol Metabolism in diabetes mellitus. Proc. Natl. Acad. Sci. U.S.A. 1993 90: 9988–92.

14. Ortmeyer H K, Bodkin N L, Lilley K, Larner J, Hansen B C. 1993 Chiroinositol deficiency and insulin resistance I. Urinary secretion rate of chiroinositol is directly associated with insulin resistance in spontaneously diabetic rhesus monkeys. Endocrinology. 132: 640–645.

15. Ortmeyer H K, Huang L C, Zhang L, Hansen B C, Larner J. 1993 Chiroinositol deficiency and insulin resistance. II. Acute effects of D-chiroinositol administration in streptozotocin-diabetic rats, normal rats given a glucose load, and spontaneously insulin-resistant rhesus monkeys. Endocrinology. 132: 646–651.

APPENDIX 1

1. IPG Hydrolisis

IPGs (LIA, LCA, LIP, LCP and blank), about the material obtained from 1 rat liver, was treated with 2N HCl (Pierce, extracted with dithizone as described below)@ 110° C. for 90 min. After hydrolisis, the samples were freeze dried twice, redissolved in $H_2O$ (200 $\mu$l) and freeze dried once more. The material obtained was redissolved in 200 $\mu$l ($H_2O$) and 10 $\mu$l samples were used to investigate the presence of inositols, monosaccharides and metals as described.

2. Dithizone Treatment of HCl

Diphenylthiocarbazone (Aldrich) was recrystallised from chloroform as described (Zief and Mitchel, p127). The crystalline purified dithizone was then dissolved in $Cl_3CH$ @ 10 mg/10 ml and used to extract metal contamination from 6N HCl, constant boiling point (Pierce).

1 ml of HCl was extracted with 500 $\mu$l of dithizone solution three times and then used to hydrolise IPGs as described above.

3. Placental IPGs. Extraction with Dithizone

50 $\mu$l of stock PGs solution were diluted to 200 $\mu$l with $H_2O$ and then extracted with 200 $\mu$l of dithizone solution in chloroform (0.1 g/l). (The chloroform used was extracted with $H_2O$/1N NaOH/$H_2O$ just before preparing the dithizone solution.)

After extracting the IPG solution with dithizone (twice), the aqueous phase was extracted with $Cl_3CH$ (200 $\mu$l, three times). The organic phases were pooled and then washed with water, then dried and redissolved in $Cl_3CH$ (200 $\mu$l). The solution was extracted with 3N HCl (100 $\mu$l) to determine metals.

The original aqueous IPS solution was used to determine changes in the Dionex Profile and PDH assay.

4. Dionex Methods

| IPGs | |
| --- | --- |
| Column and Guard Column: | PA100 |
| Eluants: | A = 100 mM NaOH |
| | B = 500 mM NaOAc + 100 mM NaOH |
| Gradient: | |
| @ initial: | 100% A, 0% B |

-continued

IPGs

| | |
|---|---|
| @ 30 min: | 25% A, 75% B |
| @ 30.1 min: | 100% A maintained for 10 min |
| Flow rate: | 1 ml/min |
| Detector: | ED40 |

5. Metal Analysis

| | |
|---|---|
| Column and Guard Column: | HPIC-CS5 |
| Eluent: | PDCA (6 mm PCDA, 50 mM AcOH, 5O mM NaOAc, PH 4.57) |
| Flow rate: | 1 ml/min |
| Post Column reagent: | 0.3 mM PAR, 1M AcOH, 3M $NH_4OH$ |
| Reagent flow rate: | ~0.8 ml/min |
| Detector AD40 @ 520 mm | |

6. Inositol Analysis

| Column and Guard Column = CarboPac MAl | | | |
|---|---|---|---|
| Eluents: | A = 500 mM NaOH | | |
| | B = $H_2O$ | | |
| Conditions: | | | |
| Time | Flow | % A | % B |
| Initial | 0.25 | 25 | 75 |
| 0.00 | 0.25 | 25 | 75 |
| 15.10 | 0.25 | 25 | 75 |
| 20 | 0.40 | 100 | 0 |
| 25 | 0.40 | 100 | 0 |
| 34 | 0.40 | 25 | 0 |
| 35 | 0.40 | 25 | 75 |
| 40 | 0.40 | 25 | 75 |
| Detector: | ED4O | | |

7. Monosaccharide Analysis

| Detector: ED4O | | |
|---|---|---|
| Column and Guard Column = Carbo Pac PA1 | | |
| Eluents: | A = 100 mM NaOH; B = $H_2O$ | |
| Conditions: | Flow rate: 1 ml/min | |
| Time | % A | % B |
| Initial | 16 | 84 |
| 0 | 16 | 84 |
| 17 | 16 | 84 |
| 18 | 100 | 0 |
| 23 | 100 | 0 |
| 24 | 16 | 84 |
| 30 | 16 | 84 |

TABLE 1

Bioactivity of Mediators Per Tissue Weight

| | milliunits/g liver† | |
|---|---|---|
| | PDH phosphatase (stimulating activity) | Lipogenesis (lipogenic activity) |
| §Human liver (10 mM Fraction) | 1960 [N] 1650 [D] | no activity [N] no activity [D] |
| Human liver (50 mM Fraction) | 600 [N] 700 [D] | 2640 ± 231 (n = 3) [N] 551 ± 119 (n = 7) [D] |
| Human placenta (10 mM Fraction) | 28100 | — |
| Human placenta (50 mM Fraction) | — | no activity |
| ‡Rat liver (10 mM Fraction) (no insulin) | 1992 ± 157 (n = 3) | no activity |
| Rat liver (10 mM Fraction) (plus insulin) | 3480 ± 300 (n = 4) | no activity |
| Rat liver (50 mM Fraction) (no insulin) | 1280 | 1676 ± 115 (n = 2) |
| Rat liver (50 mM Fraction) (plus insulin) | 1090 | 222 ± 447 (n = 3) |
| ¥Insulin (1 nM) | | 5160 ± 310 (n – 20) |

Footnotes to Table 1.
†Unit of activity: A unit of activity is defined as the amount causing a 50% activation in the basal level of the test system.
‡For the rat liver data the n value represents different independent extractions of separate liver preparations. Normally two animals (livers) were pooled prior to an extraction. Each lipogenesis assay was performed in triplicate. Two separate values are given, for control or sham injected rats or for livers extracted 2 minutes after an injection of 50 munits of insulin. Both groups were starved overnight.
¥The insulin value is for twenty independent lipogenesis assays (each measured in triplicate) performed over the period October 1994 to October 1995.
§The values for human liver are from two separate livers, [N] normal and [D] diseased. The diseased liver was obtained at the time of liver transplant. The normal liver was from a young healthy accident victim. The n values refer to repeat lipogenic assays. Separate extracts of the diseased liver which was kept frozen at −80° C. were assayed over a one year period. No change in activity was found.

TABLE 2

Recovery of IPG from Affinity Supports

| | |
|---|---|
| Control (cpm) | 209 ± 79* |
| 10% FCS (cpm) | 46313 ± 10231 |
| A-type (cpm) | 33917 ± 6697 |
| P-type (cpm) | 36542 ± 2278 |
| C-18 (% recovery)† | |
| A-type | 86 |
| P-type | 55# |
| Blank (cpm) | 1377 ± 317∫ |
| AG3 (% recovery)† | |
| A-type | 11 |
| P-type | 1.5 |
| Blank (cpm) | 505 ± 61∫ |
| AG5O (% recovery)† | |
| A-type | 1.5 |
| P-type | 2 |
| Blank (cpm) | 258 ± 114∫ |

Footnotes
†³H-thymidine incorporation into the EGFR-transfected fibroblasts. A and P type mediators were eluted with water from the different supports. Final concentration of IPG was a 1/40 dilution of stock (see Materials and Methods). Similar results were obtained for dilutions of 1/80. All IPG stimulations were dose dependent.
Partial recovery of the P-type was consistently observed on C-18. No attempt was made to recover the bound material.
∫Blank - Column eluate prior to elution of IPG.
*Control - Cultural medium only, no FCS.

What is claimed is:

1. An isolated P-type substance as obtainable from human liver or placenta, wherein the substance is a cyclitol containing carbohydrate comprising $Mn^{2+}$ and $Zn^{2+}$ ions and has the biological activity of activating pyruvate dehydrogenase (PDH) phosphatase.

2. An isolated P-type substance which is a cyclitol containing carbohydrate, said substance comprising $Mn^{2+}$ and $Zn^{2+}$ ions, as obtainable from human liver or placenta by:
   (a) making an extract by heat and acid treatment of a liver or placenta homogenate, the homogenate being processed from tissue immediately frozen in liquid nitrogen;
   (b) centrifuging the extract to produce a first supernatant, treating the first supernatant with charcoal, recentrifuging the treated first supernatant to produce a second supernatant, and treating the second supernatant overnight with an AG1-X8 anion exchange resin to produce a second supernatant/resin solution;
   (c) pouring the second supernatant/resin solution into a column and eluting the P-substance from the column with 10 mM HCl to produce an acid eluate containing the P-type substance;
   (d) neutralising the acid eluate to between pH 4 and pH 7.8 and lyophilising the neutralized acid eluate to produce a first preparation containing the P-type substance;
   (e) subjecting the first preparation to descending paper chromatography using 4/1/1 butanol/ethanol/water as solvent to obtain a second preparation containing the P-type substance;
   (f) subjecting the second preparation to high voltage paper electrophoresis in pyridine/acetic acid/water to obtain a third preparation containing the P-type substance; and,
   (g) further purifying the P-type substance by subjecting the third preparation to Dionex anion exchange chromatography and/or isolating the P-type substance using Vydac HPLC chromatography.

3. An isolated substance which is a P-type cyclitol containing carbohydrate comprising $Mn^{2+}$ and $Zn^{2+}$ ions and has the biological activity of activating pyruvate dehydrogenase (PDH) phosphatase, wherein the substance has a molecular weight determined using negative mode MALDI mass spectroscopy as shown in FIG. 11, or a molecular weight related to one of the molecular weights set out in FIG. 11 by the addition or subtraction of one or more structure units of about 236 m/z.

4. The substance of claim 1, wherein the substance comprises phosphate.

5. The substance of claim 1, wherein the substance has one or more of the following properties:
   (a) the substance migrates near the origin in descending paper chromatography using 4/1/1 butanol/ethanol/water as a solvent;
   (b) the substance is partially retained on C-18 affinity resin;
   (c) the substance is bound on Dowex AG50 cation exchange resin;
   (d) the substance is bound on an AG3A anion exchange resin; or,
   (e) the substance has an activity that is resistant to pronase.

6. The substance of claim 1, wherein the substance:
   (a) stimulates glycogen synthase phosphatase activity; or
   (b) is mitogenic when added to fibroblasts in serum free medium.

7. A pharmaceutical composition comprising the substance of claim 1, in combination with a pharmaceutically acceptable carrier.

8. The pharmaceutical composition of claim 7, further comprising an A-type substance or insulin.

9. The substance of claim 2, wherein the substance comprises phosphate.

10. The substance of claim 3, wherein the substance comprises phosphate.

11. The substance of claim 2 wherein the substance has one or more of the following properties:
    (a) the substance migrates near the origin in descending paper chromatography using 4/1/1 butanol/ethanol/water as a solvent;
    (b) the substance is partially retained on C-18 affinity resin;
    (c) the substance is bound on Dowex AG50 cation exchange resin;
    (d) the substance is bound on AG3A anion exchange resin; or
    (e) the substance has an activity that is resistant to pronase.

12. The substance of claim 3 wherein the substance has one or more of the following properties:
    (a) the substance migrates near the origin in descending paper chromatography using 4/1/1 butanol/ethanol/water as a solvent;
    (b) the substance is partially retained on C-18 affinity resin;
    (c) the substance is bound on Dowex AG50 cation exchange resin;
    (d) the substance is bound on AG3A anion exchange resin; or
    (e) the substance has an activity that is resistant to pronase.

13. The substance of claim 3 wherein the substance has one or more of the following properties:
    (a) the substance migrates near the origin in descending paper chromatography using 4/1/1 butanol/ethanol/water as a solvent;
    (b) the substance is partially retained on C-18 affinity resin;
    (c) the substance is bound on Dowex AG50 cation exchange resin;
    (d) the substance is bound on AG3A anion exchange resin; or
    (e) the substance has an activity that is resistant to pronase.

14. The pharmaceutical composition comprising the substance of claim 2, in combination with a pharmaceutically acceptable carrier.

15. The pharmaceutical composition comprising the substance of claim 3, in combination with a pharmaceutically acceptable carrier.

16. The pharmaceutical composition comprising the substance of claim 4, in combination with a pharmaceutically acceptable carrier.

17. The pharmaceutical composition comprising the substance of claim 9, in combination with a pharmaceutically acceptable carrier.

18. The pharmaceutical composition comprising the substance of claim 10, in combination with a pharmaceutically acceptable carrier.

19. The pharmaceutical composition of claim 14, further comprising an A-type substance or insulin.

20. The pharmaceutical composition of claim 15, further comprising an A-type substance or insulin.

21. The pharmaceutical composition of claim 16, further comprising an A-type substance or insulin.

22. The pharmaceutical composition of claim 17, further comprising an A-type substance or insulin.

23. The pharmaceutical composition of claim 18, further comprising an A-type substance or insulin.

* * * * *